ns011499980B2

(12) United States Patent
Sommer et al.

(10) Patent No.: US 11,499,980 B2
(45) Date of Patent: Nov. 15, 2022

(54) METHOD FOR MEASURING TEAR CONSTITUENTS IN A TEAR SAMPLE

(71) Applicant: Diagnostear, Ltd., Tel Aviv (IL)

(72) Inventors: Amos Sommer, Herzliya (IL); Ouriel Faktor, Herzliya (IL); Eran Eilat, Herzliya (IL)

(73) Assignee: Diagnostear, Ltd., Tel Aviv (IL)

( * ) Notice: Subject to any disclaimer, the term of this patent is extended or adjusted under 35 U.S.C. 154(b) by 496 days.

(21) Appl. No.: 16/733,328

(22) Filed: Jan. 3, 2020

(65) Prior Publication Data

US 2020/0141945 A1    May 7, 2020

Related U.S. Application Data

(62) Division of application No. 15/570,163, filed as application No. PCT/IB2016/000658 on May 2, 2016, now Pat. No. 10,527,628.

(Continued)

(51) Int. Cl.
*G01N 33/68* (2006.01)
*G01N 33/573* (2006.01)

(52) U.S. Cl.
CPC ....... *G01N 33/6827* (2013.01); *G01N 33/573* (2013.01); *G01N 2333/765* (2013.01);
(Continued)

(58) Field of Classification Search
CPC ............. G01N 33/6827; G01N 33/573; G01N 2333/765; G01N 2333/79;
(Continued)

(56) References Cited

U.S. PATENT DOCUMENTS

| 4,015,462 A | 4/1977 | Greyson |
| 5,006,310 A | 4/1991 | Gin et al. |

(Continued)

FOREIGN PATENT DOCUMENTS

| CA | 2216189 A1 | 5/1999 |
| EP | 0 236 023 A2 | 9/1987 |

(Continued)

OTHER PUBLICATIONS

Hashimoto, "A new schirmer test using phenol-red paper strip", Folia Ophthalmologica Japonica 14.10 (1963), pp. 337-347, English language abstract.

(Continued)

*Primary Examiner* — Jennifer Wecker
*Assistant Examiner* — Michael Paul Shimek
(74) *Attorney, Agent, or Firm* — Greenberg Traurig LLP; Barry Schindler; Natalie Salem

(57) ABSTRACT

The present invention provides a method, wherein the method classifies a subject as suffering from dry eye, the method consisting of: a. obtaining demographic data, consisting of the age and gender of the subject; b. obtaining a tear sample from the patient, and determining the level of human serum albumin; c. from the determined level of human serum albumin, assigning a score for the determined amount of human serum albumin; and d. from the assigned score, calculating a cutoff probability score, according to the following equation:

$$\frac{\exp(-0.6491 - 1.1142 * \text{Albumin})}{1 + \exp(-0.6491 - 1.1142 * \text{Albumin})}$$

(Continued)

wherein the subject has dry eye, if the calculated cutoff probability score is from 50% to 60%.

8 Claims, 6 Drawing Sheets

Related U.S. Application Data

(60) Provisional application No. 62/278,814, filed on Jan. 14, 2016, provisional application No. 62/278,805, filed on Jan. 14, 2016, provisional application No. 62/156,072, filed on May 1, 2015, provisional application No. 62/156,093, filed on May 1, 2015, provisional application No. 62/156,087, filed on May 1, 2015, provisional application No. 62/156,079, filed on May 1, 2015.

(52) U.S. Cl.
CPC ... *G01N 2333/79* (2013.01); *G01N 2333/936* (2013.01); *G01N 2800/162* (2013.01)

(58) Field of Classification Search
CPC ....... G01N 2333/936; G01N 2800/162; G01N 33/68; G01N 2800/16
See application file for complete search history.

(56) References Cited

U.S. PATENT DOCUMENTS

| | | | |
|---|---|---|---|
| 5,170,799 A | 12/1992 | Nagase et al. |
| 5,260,069 A | 11/1993 | Chen |
| 5,352,411 A | 10/1994 | Khuri |
| 5,435,970 A | 7/1995 | Mamenta et al. |
| 5,691,207 A | 11/1997 | Holtlund et al. |
| 5,744,096 A | 4/1998 | Jones et al. |
| 5,948,894 A | 9/1999 | Berry et al. |
| 7,129,717 B2 | 10/2006 | Donsky |
| 7,134,998 B2 | 11/2006 | Endo et al. |
| 7,374,719 B2 | 5/2008 | Anaokar |
| 8,206,944 B2 | 6/2012 | Clausen |
| 8,323,903 B2 | 12/2012 | Archer et al. |
| 8,377,684 B2 | 2/2013 | Bae et al. |
| 8,475,808 B2 | 7/2013 | Andrews et al. |
| 10,527,628 B2 | 1/2020 | Sommer et al. |
| 2002/0182600 A1 | 12/2002 | Smith |
| 2004/0076547 A1 | 4/2004 | Carney et al. |
| 2005/0003523 A1 | 1/2005 | Anaokar |
| 2005/0214161 A1 | 9/2005 | Gupta |
| 2005/0249633 A1 | 11/2005 | Blatt |
| 2007/0140911 A1 | 6/2007 | Carney |
| 2008/0038759 A1 | 2/2008 | Keren et al. |
| 2010/0068797 A1 | 3/2010 | Hubscher |
| 2011/0039290 A1 | 2/2011 | Clausen |
| 2011/0252872 A1 | 10/2011 | Ding |
| 2012/0171221 A1 | 7/2012 | Hamm-Alvarez et al. |
| 2014/0314715 A1 | 10/2014 | Baban et al. |
| 2014/0357971 A1 | 12/2014 | Eilat et al. |
| 2019/0212342 A1 | 7/2019 | Sommer et al. |

FOREIGN PATENT DOCUMENTS

| | | | |
|---|---|---|---|
| EP | 0 442 231 A1 | 8/1991 |
| EP | 1692999 A1 | 8/2006 |
| EP | 2603797 B1 | 4/2017 |
| SU | 1534406 A1 | 1/1990 |
| WO | 95/05593 A1 | 2/1995 |
| WO | 2008073399 A1 | 6/2008 |
| WO | 2012020046 A1 | 2/2012 |
| WO | 2013080196 A1 | 6/2013 |
| WO | 2013/162456 | 10/2013 |
| WO | 2016/178083 | 11/2016 |

OTHER PUBLICATIONS

Mackie et al., "Diagnostic implications of tear protein profiles", British Journal of Ophthalmology, 1984, 68, pp. 321-324.

Farris et al., "Tear Osmolarity Variation in the Dry Eye", Trans. Am. Ophthalmol. Soc., vol. 84, 1986, pp. 250-268.

Seal et al., "Quantitative tear lysozyme assay: a new technique for transporting specimens", British Journal of Ophthalmology, 1980, 64, pp. 700-704.

Savini et al., "The challenge of dry eye diagnosis", Clinical Ophthalmology 2008:2(1), pp. 31-55.

Methodologies to diagnose and monitor dry eye disease: report of the Diagnostic methodology Subcommitee of the International Dry Eye Workshop (2007). Ocul Surf. Apr. 2007;5(2)L 108-52.

Chiva, Andreea. "Electrophoresis of Tear Proteins as a New Diagnostic Tool for Two High Risk Groups for Dry Eye: Computer Users and Contact Lens Wearers." J. Med Life. Aug. 15, 2011; 4(3): 228-233. Published online Aug. 25, 2011.

Versura, et al., "A rapid standardized quantitative microfluidic system approach for evaluating human tear proteins", Molecular Vision, vol. 18, pp. 2526-2537, Jan. 1, 2012.

Bron, AJ et al. Methodologies to diagnose and monitor dry eye disease: Report of the Diagnostic Methodology Subcommittee of the International Dry Eye Work Shop (2007). The Ocular Surface. vol. 5. No. 2 (2007): 108-152; abstract; table 2; p. 114, col. 1, paragraphs 1-4.

Guerra, MA et al. "Quantitative approach for the serodiagnosis of canine Lyme disease by the immunoblot procedure." Journal of clinical microbiology. vol. 38. No. 7 (2000): 2628-2632; p. 2630; col. 2, paragraph 2.

Vianelli, A et al. Bacteriophage T4 self-assembly: localization of gp3 and its role in determining tail length. Journal of bacteriology. vol. 182. No1 3 (2000): 680-688; p. 682, col. 1, paragraphs 1-2; p. 682, col. 2, paragraph 2.

Margraf-Schonfeld, S et al., Glycosylation affects ligand binding and function of the activating natural killer cell receptor 2B4 (CD244) protein. Journal of Biological Chemistry. vol. 286. No. 27(2011): 24142-24149; figure 6; p. 5, col. 1, paragraph 3; p. 9. paragraph 6.

International search Report and Written Opinion from International Application No. PCT/IB2016/000658 dated Oct. 24, 2016.

Li et al., "Quantification of tear proteins and sPLA2-IIa alteration in patients with allergic conjunctivitis"; Molecular Vision 2010; 16: 2084-2091.

Srinivasan et al., "iTRAQ Quantitative Proteomics in the Analysis of Tears in Dry Eye Patients"; Investigative Ophthalmology & Visual Science, Jul. 2012, vol. 53, No. 8: 5052-5059.

Vesura et al., "Diagnostic performance of a tear protein panel in early dry eye"; Molecular Vision 2013; 19: 1247-1257.

Laudy, et al., "Importance of the lacrymal levels (total IgE, specific IgE and albumin) for the study of allergic conjunctivitis", Allerg Immunol (Paris). vol. 26, No. 3, pp. 95-96, Mar. 1994. (Abstract Only).

| Analyte/<br>concentration | | | | | | | | | |
|---|---|---|---|---|---|---|---|---|---|
| Lactoferrin ug/ml | 1 | 4 | 12.5 | 25 | 50 | 75 | 100 | 150 | 200 |

0.1   0.25   0.5   0.75 1.0   1.25   1.5   1.75   2.0

| Analyte/concentration | | | | | | | | |
|---|---|---|---|---|---|---|---|---|
| Human Serum Albumin [HAS] ug/ml | 0 | 0.1 | 0.5 | 0.75 | 1 | 1.1 | 1.2 | 6 | 10 |

0.1   0.25   0.5   0.75   1.0   1.25   1.5   1.75   2.0

| Analyte/ concentration | | | | | | | | |
|---|---|---|---|---|---|---|---|---|
| Lysozyme ug/ml | 0 | 1 | 3 | 12 | 25 | 40 | 70 | 100 | 150 |

| Analyte/<br>concentration | | | | | | | | |
|---|---|---|---|---|---|---|---|---|
| Mucin<br>ug/ml | 0 | 0.1 | 0.5 | 1 | 3 | 6 | 12 | 25 | 50 |

METHOD FOR MEASURING TEAR CONSTITUENTS IN A TEAR SAMPLE

CROSS REFERENCE TO RELATED APPLICATIONS

This application a divisional of U.S. application Ser. No. 15/570,163, filed Oct. 27, 2017, which is a National Phase application under 35 U.S.C. 371 of International Application No. PCT/IB2016/000658, filed May 2, 2016, which claims priority to U.S. Provisional Patent Application Ser. No. 62/156,072, filed on May 1, 2015; U.S. Provisional Patent Application Ser. No. 62/156,079, filed on May 1, 2015; U.S. Provisional Patent Application Ser. No. 62/156,087, filed on May 1, 2015; U.S. Provisional Patent Application Ser. No. 62/156,093, filed on May 1, 2015; U.S. Provisional Patent Application Ser. No. 62/278,805, filed on Jan. 14, 2016; and U.S. Provisional Patent Application Ser. No. 62/278,814, filed on Jan. 14, 2016, the entire contents of which each of are hereby incorporated by reference in their entirety.

FIELD OF THE INVENTION

The present invention generally relates to diagnostic methods and devices and in particular, to methods and devices for diagnosing dry eye syndrome.

BACKGROUND

Dry Eye Syndrome is a disorder of the tear film resulting from tear deficiency which causes discomfort and damage to the inter-palpebral ocular surface. Tears are an extracellular fluid covering the surface epithelial cells of the corneal and conjunctival epithelium. The functions of the tear film include lubrication the surface of the eye and the eyelids, optimizing the refractive function of the anterior segment, and providing a means for removal of environmental contaminants from the ocular surface.

The normal tear film is composed of three layers: an outer lipid layer (approximately 0.1 µm thick) produced by the meibomian glands in the tarsal plate, a central aqueous layer (approximately 7-10 µm thick) produced by both the main and accessory lacrimal glands, and an inner mucin layer (approximately 0.2-1.0 µm thick) produced by goblet cells in the conjunctiva. The list of tear components includes water, electrolytes, lipids, and proteins (such as lipocalin, lactoferrin, mucins, and lysozyme), as well as various immunoglobins, growth factors and cytokines. When the quality or quantity of tears is compromised by an imbalance or breakdown in these components, it can severely impact the eye and cause or exacerbate dry eye symptoms.

SUMMARY

In one embodiment, the present invention provides a method, wherein the method classifies a subject as suffering from dry eye, the method consisting of:
a. obtaining demographic data, consisting of the age and gender of the subject;
b. obtaining a tear sample from the patient, and determining the level of human serum albumin;
c. from the determined level of human serum albumin, assigning a score for the determined amount of human serum albumin; and
d. from the assigned score, calculating a cutoff probability score, according to the following equation:

$$\frac{\exp(-0.6491 - 1.1142 * \text{Albumin})}{1 + \exp(-0.6491 - 1.1142 * \text{Albumin})}$$

wherein the subject has dry eye, if the calculated cutoff probability score is from 50% to 60%.

In one embodiment, the method has a cutoff probability score of 50%, and correctly classifies subjects as having dry eye 77% of the time and correctly classifies subjects as healthy 30% of the time.

In one embodiment, the method has a cutoff probability score of 60%, and correctly classifies subjects as having dry eye 68% of time and correctly classifies subjects as healthy 63% of the time.

In one embodiment, the determining of the level of the human serum albumin is performed using an immunochemical reaction, configured to produce a color, wherein the intensity of the color is proportional to the amount of the human serum albumin in the tear sample, and wherein the score is assigned according to intensity of the color.

In one embodiment, the present invention provides a device for determining the level of human serum albumin, the device comprising:
a. a test strip configured to receive a tear sample from the patient; and
b. a reagent pad, containing reagents specific for human serum albumin, that, upon contact with the tear sample, undergo a reaction configured to produce a color, wherein the intensity of the color is proportional to the amount of human serum albumin in the tear sample, and wherein the test strip is configured to deliver the tear sample to the reagent pad.

In one embodiment, the present invention provides a method, wherein the method classifies a subject as suffering from dry eye, the method consisting of:
a. obtaining demographic data, consisting of the age and gender of the subject;
b. obtaining a tear sample from the patient, and determining the level of human serum albumin, lactoferrin, and lysozyme;
c. from the determined level of human serum albumin, lactoferrin, and lysozyme, assigning a score for the determined amount of human serum albumin, lactoferrin, and lysozyme; and
d. from the assigned score, calculating a cutoff probability score, according to the following equation:

$$\frac{\exp\begin{pmatrix} -5.7198 - 3.9059*\text{Albumin} - 0.7375*\text{Lysozyme} - \\ 2.7929*\text{Lactoferrin} + 0.1507*\text{Age}(yrs) + 1.2206* \\ (-1 \text{ if male}) + 7.1682*\text{Albumin}*\text{Lactoferrin} + 4.4090* \\ \text{Albumin}*\text{Lysozyme} - 10.7566*\text{Lysozyme}*\text{Lactoferrin} \end{pmatrix}}{1 + \exp\begin{pmatrix} -5.7198 - 3.9059*\text{Albumin} - 0.7375*\text{Lysozyme} - \\ 2.7929*\text{Lactoferrin} + 0.1507*\text{Age}(yrs) + 1.2206* \\ (-1 \text{ if male}) + 7.1682*\text{Albumin}*\text{Lactoferrin} + \\ 4.4090*\text{Albumin}*\text{Lysozyme} - \\ 10.7566*\text{Lysozyme}*\text{Lactoferrin} \end{pmatrix}}$$

wherein the subject has dry eye, if the calculated cutoff probability score is from 50% to 60%.

In one embodiment, the method has a cutoff probability score of 50% and correctly classifies subjects as having dry eye 88% of time and correctly classifies subjects as healthy 76% of the time.

In one embodiment, the method has a cutoff probability score of 55% and correctly classifies subjects as having dry eye 84% of time and correctly classifies subjects as healthy 80% of the time.

In one embodiment, the method has a cutoff probability score of 60% and correctly classifies subjects as having dry eye 81% of time and correctly classifies subjects as healthy 86% of the time.

In one embodiment, the present invention provides a device for determining the level of at least one tear constituent selected from the group consisting of: human serum albumin, lactoferrin, and lysozyme, the device comprising:
  a. a test strip configured to receive a tear sample from the patient; and
  b. a plurality of reagent pads, wherein a first individual reagent pad contains reagents specific for human serum albumin, a second reagent pad contains reagents specific for lysozyme, and a third reagent pad contains reagents specific for lactoferrin, wherein the reagents in the first, second and third reagent pads, upon contact with the tear sample, undergo a reaction configured to produce a color, wherein the intensity of the color is proportional to the amount of the human serum albumin, lysozyme, and lactoferrin present in the tear sample, and wherein the test strip is configured to deliver the tear sample to the plurality of reagent pads.

DETAILED DESCRIPTION

For clarity of disclosure, and not by way of limitation, the detailed description of the invention is divided into the following subsections that describe or illustrate certain features, embodiments or applications of the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "a dry eye disease" refers a disorder of the tear film resulting from tear deficiency which causes discomfort and damage to the inter-palpebral ocular surface. In some embodiments of the method of the present invention, the dry eye disease can be caused by, but not limited to, exacerbation by environmental conditions, by lifestyle choices, or by medications.

As used herein, the term "effective volume," when used to describe tears collected in some methods of the embodiments of the invention disclosed herein, refers to a volume large enough to provide a definitive result when subjected to a particular chemical or physical test. Thus, the "effective volume" will depend on the particular test being performed.

As used herein, the term "lysozyme" refers to a protein synthesized and secreted by the acini of the lacrimal gland. The amount of lysozyme present in normal tears ranges from 0.6-2.6 mg/ml, where it acts as an antibacterial by degrading cell wall components of bacteria in the tear film.

As used herein, the term "mild dry eye" refers to transient symptoms or signs of the disease that do not require treatment, as diagnosed by a patient and/or a medical professional (e.g., but not limited to, a doctor, a nurse, etc.). For dry eye to be considered moderate, patients must experience signs or symptoms that are responsive to simple therapeutic measures (e.g., but not limited to, applying eye drops to the dry eye(s)).

Figure 1:
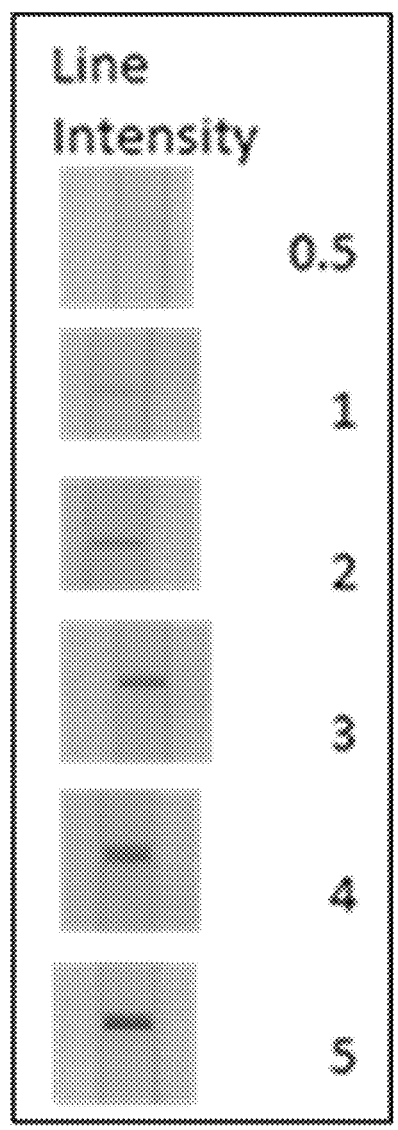
FIG. 1 shows the correlation of test line intensity obtained using a lactoferrin assay according to some embodiments of the present invention
Figure 2:
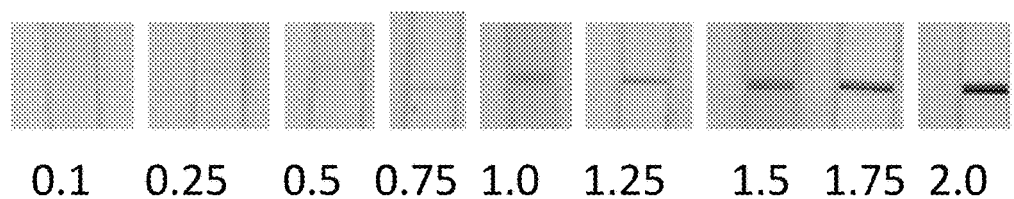
FIG. 2 shows the correlation of test line intensity obtained using a lactoferrin assay according to some embodiments of the present invention with analyte concentration.

As used herein, the term "semi-quantitative intensity measurement" refers to a result obtained from an assay, where the assay includes a fixed running time and use of a test strip(s) configured to receive a tear containing at least one tear constituent (e.g., lysozyme) by a medical professional, and where a medical professional compares the line intensity of the test strip (i.e., a tear analyzing strip) to a control printed picture containing a panel of lines intensities (e.g., as shown in FIGS. 1 and 2) (referred to wherein as "a scale panel") containing a plurality of line intensities so as to determine whether the intensity result of the test strip indicates that a subject has a dry eye disease. This semi-quantitative intensity measurement can be used for comparison and correlation to other tests, such as the Schirmer's test, TFBUT, OSDI, corneal staining, or any combination thereof. In some embodiments, the scale panel is a printed picture of a plurality of color line intensities.

As used herein, the term "tear(s)" refer(s) to an extracellular fluid covering the surface epithelial cells of the corneal and conjunctival epithelium, where the tear film represents the last line of defense for the ocular surface. The primary functions of the tear film are to lubricate the surface and the lids, to optimize the refractive function of the anterior segment, and to provide a means for removal of environmental contaminants from the ocular surface. The normal tear film is composed of three layers: an outer lipid layer (approximately 0.1 μm thick) produced by the meibomian glands in the tarsal plate, a central aqueous layer (approximately 7-10 μm thick) produced by both the main and accessory lacrimal glands, and an inner mucin layer (approximately 0.2-1.0 μm thick) produced by goblet cells in the conjunctiva.

As used herein, the term "tear components" refer to the molecules in tears and includes, but is not limited to, water, electrolytes, antimicrobial molecules, immunoglobulins, mucins, lipids, growth factors, or any combination thereof. When the quality or quantity of tears is compromised by an imbalance or breakdown in any of these components, the result can be a cause or exacerbation of dry eye symptoms.

In some embodiments of the method of the present invention, the following is a list of terms and accompanying abbreviations of the terms used herein:

| Abbreviation | Term |
| --- | --- |
| AE | adverse event |
| BCA | bicinchoninic acid, reagent for protein determination |
| CAE | controlled adverse environment |
| DE | dry eye |
| ETDRS | Early Treatment of Diabetic Retinopathy Study |
| FDA | Food and Drug Administration |
| g | Gram |
| IOP | intraocular pressure |
| IRB | institutional/independent review board |
| IU | international unit |
| IV | Intravenous |
| kg | Kilogram |
| logMAR | logarithm of the minimum angle of resolution |
| MedDRA | Medical Dictionary for Regulatory Activities |
| mg | Milligram |
| μg | Microgram |
| ml | Milliliter |
| μl | microliter |
| mm | Millimeter |
| μm | Micrometer |
| OSDI | Ocular surface disease index |
| PBS | Phosphate-buffered saline |
| TFBUT | Tear film break-up time |
| Schirmer's | Schirmer's test |

In some embodiments, the present invention provides a method, wherein the method classifies a subject as suffering from dry eye, the method consisting of:
  a. obtaining demographic data, consisting of the age and gender of the subject;
  b. obtaining a tear sample from the patient, and determining the level of at least one tear constituent selected from the group consisting of: human serum albumin, lactoferrin, lysozyme, and mucin;
  c. from the determined amount, assigning a score for the level of the at least one tear constituent and
  d. from score for the at least one tear constituent, calculating a cutoff probability score,
    wherein the subject has dry eye, if the calculated cutoff probability score is from 50% to 60%.

In some embodiments, the determining of the level of the at least one tear constituent is performed using an immunochemical reaction, configured to produce a color, wherein the intensity of the color is proportional to the amount of the at least one tear constituent in the tear sample, and wherein the score is assigned according to intensity of the color.

In some embodiments, the score selected from the group consisting of: 0.25, 0.5, 0.75, 1.0, 1.25, 1.5, 1.75, and 2.0.

In some embodiments, the present invention provides a method, wherein the method classifies a subject as suffering from dry eye, the method consisting of:
  a. obtaining demographic data, consisting of the age and gender of the subject;
  b. obtaining a tear sample from the patient, and determining the level of human serum albumin;
  c. from the determined level of human serum albumin, assigning a score for the determined amount of human serum albumin; and
  d. from the assigned score, calculating a cutoff probability score, according to the following equation:

$$\frac{\exp(-0.6491 - 1.1142*\text{Albumin})}{1 + \exp(-0.6491 - 1.1142*\text{Albumin})}$$

wherein the subject has dry eye, if the calculated cutoff probability score is from 50% to 60%.

In some embodiments, the method has a cutoff probability score of 50%, and correctly classifies subjects as having dry eye 77% of the time and correctly classifies subjects as healthy 30% of the time.

In some embodiments, the method has a cutoff probability score of 60%, and correctly classifies subjects as having dry eye 68% of time and correctly classifies subjects as healthy 63% of the time.

In some embodiments, the determining of the level of the human serum albumin is performed using an immunochemical reaction, configured to produce a color, wherein the intensity of the color is proportional to the amount of the human serum albumin in the tear sample, and wherein the score is assigned according to intensity of the color.

In some embodiments, the score selected from the group consisting of: 0.25, 0.5, 0.75, 1.0, 1.25, 1.5, 1.75, and 2.0.

In some embodiments, the present invention provides a method, wherein the method classifies a subject as suffering from dry eye, the method consisting of:
  a. obtaining demographic data, consisting of the age and gender of the subject;
  b. obtaining a tear sample from the patient, and determining the level of human serum albumin, lactoferrin, and lysozyme;
  c. from the determined level of human serum albumin, lactoferrin, and lysozyme, assigning a score for the determined amount of human serum albumin, lactoferrin, and lysozyme; and
  d. from the assigned score, calculating a cutoff probability score, according to the following equation:

$$\frac{\exp\begin{pmatrix}-5.7198 - 3.9059*\text{Albumin} - 0.7375*\text{Lysozyme} - \\ 2.7929*\text{Lactoferrin} + 0.1507*\text{Age}(yrs) + 1.2206* \\ (-1 \text{ if male}) + 7.1682*\text{Albumin}*\text{Lactoferrin} + 4.4090* \\ \text{Albumin}*\text{Lysozyme} - 10.7566*\text{Lysozyme}*\text{Lactoferrin}\end{pmatrix}}{1 + \exp\begin{pmatrix}-5.7198 - 3.9059*\text{Albumin} - 0.7375*\text{Lysozyme} - \\ 2.7929*\text{Lactoferrin} + 0.1507*\text{Age}(yrs) + 1.2206* \\ (-1 \text{ if male}) + 7.1682*\text{Albumin}*\text{Lactoferrin} + \\ 4.4090*\text{Albumin}*\text{Lysozyme} - \\ 10.7566*\text{Lysozyme}*\text{Lactoferrin}\end{pmatrix}}$$

wherein the subject has dry eye, if the calculated cutoff probability score is from 50% to 60%.

In some embodiments, the method has a cutoff probability score of 50% and correctly classifies subjects as having dry eye 88% of time and correctly classifies subjects as healthy 76% of the time.

In some embodiments, the method has a cutoff probability score of 55% and correctly classifies subjects as having dry eye 84% of time and correctly classifies subjects as healthy 80% of the time.

In some embodiments, the method has a cutoff probability of 60% and correctly classifies subjects as having dry eye 81% of time and correctly classifies subjects as healthy 86% of the time.

In some embodiments, the score selected from the group consisting of: 0.25, 0.5, 0.75, 1.0, 1.25, 1.5, 1.75, and 2.0.

In some embodiments, the volume of the tear sample is between 1 to 25 microliters. In some embodiments, the volume of the tear sample is 1 microliter. In some embodiments, the volume of the tear sample is 2 microliters. In some embodiments, the volume of the tear sample is 4 microliters. In some embodiments, the volume of the tear sample is 6 microliters. In some embodiments, the volume of the tear sample is 8 microliters. In some embodiments, the volume of the tear sample is 10 microliters. In some embodiments, the volume of the tear sample is 12 microliters. In some embodiments, the volume of the tear sample is 14 microliters. In some embodiments, the volume of the tear sample is 16 microliters. In some embodiments, the volume of the tear sample is 18 microliters. In some embodiments, the volume of the tear sample is 20 microliters. In some embodiments, the volume of the tear sample is 21 microliters. In some embodiments, the volume of the tear sample is 22 microliters. In some embodiments, the volume of the tear sample is 23 microliters. In some embodiments, the volume of the tear sample is 24 microliters. In some embodiments, the volume of the tear sample is 25 microliters.

Measurement of Constituents in Tear Fluid Samples According to Some Embodiments of the Present Invention In some embodiments, the present invention is a method for quantifying an amount of at least one tear constituent in a tear sample, selected from the group consisting of lysozyme, lactoferrin, mucin, human serum albumin, and any combination thereof. In some embodiments, the method is a multi-assay test.

In some embodiments, the present invention is a method for quantifying an amount of human serum albumin in a tear sample.

In some embodiments, the present invention is a method for quantifying an amount of human serum albumin and lactoferrin in a tear sample.

In some embodiments, the present invention is a method for quantifying an amount of human serum albumin, lactoferrin and lysozyme in a tear sample.

Measurement of Human Serum Albumin (HSA) in Tear Fluid Samples According to Some Embodiments of the Present Invention:

In some embodiments, the present invention is a method for quantifying an amount of Human Serum Albumin (HSA) in a tear sample, comprising: collecting the tear sample containing the amount of HSA from a subject, where the amount of HSA of the tear sample is used to generate a semi-quantitative intensity measurement of HSA by: collecting the tear sample containing the amount of HSA from the subject; contacting the tear sample containing the amount of HSA from the subject with a tear analyzing strip, where the tear analyzing strip contains 0.4 µg of at least one anti-HSA antibody (e.g. Monoclonal anti HSA clone M12619HS3, Fitzgerald Industries International, 30 Sudbury Road, Suite 1A North Acton, Mass. 01720 USA), is conjugated to colloidal gold at ratio of 0.4 ug/ml antibody to OD 1 of colloid at 526 nm, where the amount of the at least one anti-HSA antibody (e.g. Monoclonal anti HSA clone M12619HS1, Fitzgerald Industries International, 30 Sudbury Road, Suite 1A North Acton, Mass. 01720 USA), is dispensed on nitrocellulose paper at concentration of 1 mg/ml. to incubating the amount of HSA from the subject on the tear analyzing strip so as to result in a line intensity of HSA; and utilizing the line intensity of HSA to determine the semi-quantitative intensity measurement of HSA; where the semi-quantitative intensity measurement of HSA is selected from the group consisting of: 0.25, 0.5, 0.75, 1.0, 1.25, 1.5, 1.75, and 2.0.

Figure 3:
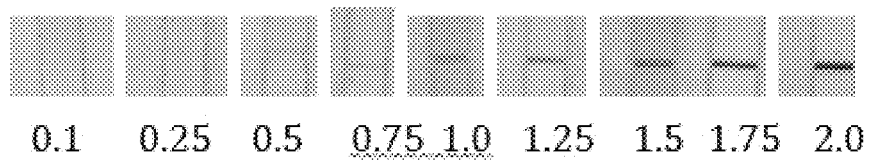
FIG. 3 shows the correlation of test line intensity obtained using a human serum albumin assay according to some embodiments of the present invention with analyte concentration.

FIG. 3 illustrates the correlation of test line intensity obtained using a human serum albumin assay according to some embodiments of the present invention with analyte concentration. In some embodiments, a reduced test line intensity correlates with an existing test for dry eye (e.g., Schirmer's test, corneal staining, OSDI, etc.).

Referring to FIG. 3, in some embodiments, an intensity of 0.1 correlates with a concentration of human serum albumin of 0 µg/ml observed in a test assay according to some embodiments of the present invention. In some embodiments, an intensity of 0.25 correlates with a concentration of human serum albumin of 0.1 µg/ml observed in a test assay according to some embodiments of the present invention. In some embodiments, an intensity of 0.5 correlates with a concentration of human serum albumin of 0.5 µg/ml observed in a test assay according to some embodiments of the present invention. In some embodiments, an intensity of 0.75 correlates with a concentration of human serum albumin of 0.75 µg/ml observed in a test assay according to some embodiments of the present invention. In some embodiments, an intensity of 1.0 correlates with a concentration of human serum albumin of 1 µg/ml observed in a test assay according to some embodiments of the present invention. In some embodiments, an intensity of 1.25 correlates with a concentration of human serum albumin of 1.1 µg/ml observed in a test assay according to some embodiments of the present invention. In some embodiments, an intensity of 1.5 correlates with a concentration of human serum albumin of 1.2 µg/ml observed in a test assay according to some embodiments of the present invention. In some embodiments, an intensity of 1.75 correlates with a concentration of human serum albumin of 6 µg/ml observed in a test assay according to some embodiments of the present invention. In some embodiments, an intensity of 2.0 correlates with a concentration of human serum albumin of 10 µg/ml observed in a test assay according to some embodiments of the present invention.

In some embodiments, the correlation of the test line indicates that a lower amount of human serum albumin on a test assay according to some embodiments of the present invention, such as, for example, 0 to 0.1 µg/ml correlates with a lower result as detected by at least one test selected from the group consisting of the Schirmer's test, the corneal staining test, ODSI, and TFBUT.

In some embodiments, the correlation of the test line indicates that a lower amount of human serum albumin on a test assay according to some embodiments of the present invention, such as, for example, 0 to 0.1 µg/ml correlates with a higher result as detected by at least one test selected from the group consisting of the Schirmer's test, the corneal staining test, ODSI, and TFBUT.

Measurement of Lactoferrin in Tear Fluid Samples According to Some Embodiments of the Present Invention:

In some embodiments, the present invention provides for a method for quantifying an amount of lactoferrin in a tear sample, comprising: collecting the tear sample containing the amount of lactoferrin from a subject, and where the amount of lactoferrin of the tear sample is used to generate a semi-quantitative intensity measurement of lactoferrin by: collecting the tear sample containing the amount of lactoferrin from the subject; contacting the tear sample containing the amount of lactoferrin from the subject with a tear analyzing strip, where the tear analyzing strip is bound to an amount of pisum stivum agglutinin (PSA) bound to biotin and an amount of lens culinaris agglutinin (LCA) (where at least the PSA is bound to nitrocellulose of the tear analyzing strip), where the amount of the PSA bound to biotin is conjugated to colloidal gold at a ratio of 2.5 µg/ml to 10 µg/ml PSA bound to biotin per 1 optical density (OD) per milliliter colloidal gold bound to streptavidin, incubating the amount of lactoferrin from the subject on the tear analyzing strip so as to result in a line intensity of lactoferrin; and utilizing the line intensity of lactoferrin to determine the semi-quantitative intensity measurement of lactoferrin; where the semi-quantitative intensity measurement of lactoferrin is selected from the group consisting of: 0.25, 0.5, 0.75, 1.0, 1.25, 1.5, 1.75, and 2.0.

In some embodiments, the ratio is 2.5 µg/ml PSA bound to biotin per 1 OD per milliliter colloidal gold bound to streptavidin. In some embodiments, the ratio is 3 µg/ml PSA bound to biotin per 1 OD per milliliter colloidal gold bound to streptavidin. In some embodiments, the ratio is 3.5 µg/ml PSA bound to biotin per 1 OD per milliliter colloidal gold bound to streptavidin. In some embodiments, the ratio is 4 µg/ml PSA bound to biotin per 1 OD per milliliter colloidal gold bound to streptavidin. In some embodiments, the ratio is 4.5 µg/ml PSA bound to biotin per 1 OD per milliliter colloidal gold bound to streptavidin. In some embodiments, the ratio is 5 µg/ml PSA bound to biotin per 1 OD per milliliter colloidal gold bound to streptavidin. In some embodiments, the ratio is 5.5 µg/ml PSA bound to biotin per 1 OD per milliliter colloidal gold bound to streptavidin. In some embodiments, the ratio is 6 µg/ml PSA bound to biotin per 1 OD per milliliter colloidal gold bound to streptavidin. In some embodiments, the ratio is 6.5 µg/ml PSA bound to biotin per 1 OD per milliliter colloidal gold bound to streptavidin. In some embodiments, the ratio is 7 µg/ml PSA bound to biotin per 1 OD per milliliter colloidal gold bound to streptavidin. In some embodiments, the ratio is 7.5 µg/ml PSA bound to biotin per 1 OD per milliliter colloidal gold bound to streptavidin. In some embodiments, the ratio is 8 µg/ml PSA bound to biotin per 1 OD per milliliter colloidal gold bound to streptavidin. In some embodiments, the ratio is 8.5 µg/ml PSA bound to biotin per 1 OD per milliliter colloidal gold bound to streptavidin. In some embodiments, the ratio is 9 µg/ml PSA bound to biotin per 1 OD per milliliter colloidal gold bound to streptavidin. In some embodiments, the ratio is 9.5 µg/ml PSA bound to biotin per 1 OD per milliliter colloidal gold bound to streptavidin. In some embodiments, the ratio is 10 µg/ml PSA bound to biotin per 1 OD per milliliter colloidal gold bound to streptavidin.

FIG. 2 illustrates the correlation of test line intensity obtained using a lactoferrin assay according to some embodiments of the present invention with analyte concentration. In some embodiments, a reduced test line intensity correlates with an existing test for dry eye (e.g., Schirmer's test, corneal staining, OSDI, etc.).

Referring to FIG. 2, in some embodiments, an intensity of 0.1 correlates with a concentration of lactoferrin of 1 µg/ml observed in a test assay according to some embodiments of the present invention. In some embodiments, an intensity of 0.25 correlates with a concentration of lactoferrin of 4 µg/ml observed in a test assay according to some embodiments of the present invention. In some embodiments, an intensity of 0.5 correlates with a concentration of lactoferrin of 12.5 µg/ml observed in a test assay according to some embodiments of the present invention. In some embodiments, an intensity of 0.75 correlates with a concentration of lactoferrin of 25 µg/ml observed in a test assay according to some embodiments of the present invention. In some embodiments, an intensity of 1.0 correlates with a concentration of lactoferrin of 50 µg/ml observed in a test assay according to some embodiments of the present invention. In some embodiments, an intensity of 1.25 correlates with a concentration of lactoferrin of 75 µg/ml observed in a test assay according to some embodiments of the present invention. In some embodiments, an intensity of 1.5 correlates with a concentration of lactoferrin of 100 µg/ml observed in a test assay according to some embodiments of the present invention. In some embodiments, an intensity of 1.75 correlates with a concentration of lactoferrin of 150 µg/ml observed in a test assay according to some embodiments of the present invention. In some embodiments, an intensity of 2.0 correlates with a concentration of lactoferrin of 200 µg/ml observed in a test assay according to some embodiments of the present invention.

In some embodiments, the correlation of the test line indicates that a lower amount of lactoferrin on a test assay according to some embodiments of the present invention, such as, for example, 1 to 4 µg/ml correlates with a lower result as detected by at least one test selected from the group consisting of the Schirmer's test, the corneal staining test, ODSI, and TFBUT.

In some embodiments, the correlation of the test line indicates that a lower amount of lactoferrin on a test assay according to some embodiments of the present invention, such as, for example, 1 to 4 µg/ml correlates with a higher result as detected by at least one test selected from the group consisting of the Schirmer's test, the corneal staining test, ODSI, and TFBUT.

Measurement of Lysozyme in Tear Fluid Samples According to Some Embodiments of the Present Invention:

In some embodiments, the present invention is a method for quantifying an amount of lysozyme in a tear sample, comprising: collecting the tear sample containing the amount of lysozyme from a subject, where the amount of lysozyme of the tear sample is used to generate a semi-quantitative intensity measurement of lysozyme by: diluting the tear sample with a dilution buffer; contacting the diluted tear sample containing the amount of lysozyme from the subject with a tear analyzing strip, wherein the tear analyzing strip contains an amount of a first antibody (such as, for example, but not limited to, a sheep or rabbit anti-lysozyme antibody) and an amount of a second antibody (such as, for example, but not limited to, a rabbit anti-lysozyme antibody), wherein the amount of the first antibody is conjugated to colloidal gold at a ratio of 2.5 µg/ml to 10 µg/ml per 1 optical density (OD) per milliliter colloidal gold, and 1.5 mg/ml of the second antibody is embedded as capture line on the tear analyzing strip, incubating the amount of lysozyme from the subject on the tear analyzing strip so as to result in a line intensity of lysozyme; and utilizing the line intensity of lysozyme to determine the semi-quantitative intensity measurement of lysozyme; wherein the semi-quantitative intensity measurement of lysozyme is selected from the group consisting of: 0.25, 0.5, 0.75, 1.0, 1.25, 1.5, 1.75, and 2.0.

In some embodiments, the ratio is 2.5 µg/ml first antibody per 1 OD per milliliter colloidal gold bound to streptavidin. In some embodiments, the ratio is 3 µg/ml first antibody per 1 OD per milliliter colloidal gold bound to streptavidin. In some embodiments, the ratio is 3.5 µg/ml first antibody per 1 OD per milliliter colloidal gold bound to streptavidin. In some embodiments, the ratio is 4 µg/ml first antibody per 1 OD per milliliter colloidal gold bound to streptavidin. In some embodiments, the ratio is 4.5 µg/ml first antibody per 1 OD per milliliter colloidal gold bound to streptavidin. In some embodiments, the ratio is 5 µg/ml first antibody per 1 OD per milliliter colloidal gold bound to streptavidin. In some embodiments, the ratio is 5.5 µg/ml first antibody per 1 OD per milliliter colloidal gold bound to streptavidin. In some embodiments, the ratio is 6 µg/ml first antibody per 1 OD per milliliter colloidal gold bound to streptavidin. In some embodiments, the ratio is 6.5 µg/ml first antibody per 1 OD per milliliter colloidal gold bound to streptavidin. In some embodiments, the ratio is 7 µg/ml first antibody per 1 OD per milliliter colloidal gold bound to streptavidin. In some embodiments, the ratio is 7.5 µg/ml first antibody per 1 OD per milliliter colloidal gold bound to streptavidin. In some embodiments, the ratio is 8 µg/ml first antibody per 1 OD per milliliter colloidal gold bound to streptavidin. In some embodiments, the ratio is 8.5 µg/ml first antibody per 1 OD per milliliter colloidal gold bound to streptavidin. In some embodiments, the ratio is 9 µg/ml first antibody per 1 OD per milliliter colloidal gold bound to streptavidin. In some embodiments, the ratio is 9.5 µg/ml first antibody per 1 OD per milliliter colloidal gold bound to streptavidin. In some embodiments, the ratio is 10 µg/ml first antibody per 1 OD per milliliter colloidal gold bound to streptavidin.

Figure 4:
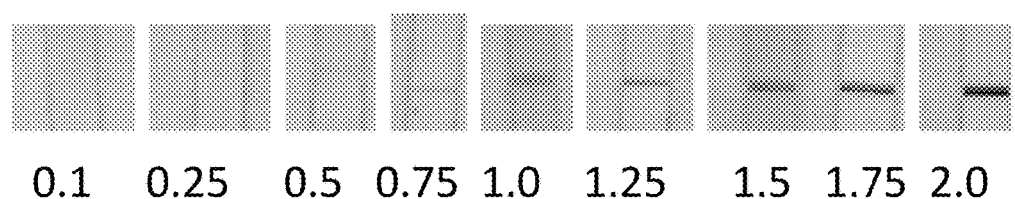
FIG. 4 shows the correlation of test line intensity obtained using a lysozyme assay according to some embodiments of the present invention with analyte concentration.

FIG. 4 illustrates the correlation of test line intensity obtained using a lysozyme assay according to some embodiments of the present invention with analyte concentration. In some embodiments, a reduced test line intensity correlates with an existing test for dry eye (e.g., Schirmer's test, corneal staining, OSDI, etc.).

Referring to FIG. 4, in some embodiments, an intensity of 0.1 correlates with a concentration of lysozyme of 0 µg/ml observed in a test assay according to some embodiments of the present invention. In some embodiments, an intensity of 0.25 correlates with a concentration of lysozyme of 1 µg/ml observed in a test assay according to some embodiments of the present invention. In some embodiments, an intensity of 0.5 correlates with a concentration of lysozyme of 3 µg/ml observed in a test assay according to some embodiments of the present invention. In some embodiments, an intensity of 0.75 correlates with a concentration of lysozyme of 12 µg/ml observed in a test assay according to some embodiments of the present invention. In some embodiments, an intensity of 1.0 correlates with a concentration of lysozyme of 25 µg/ml observed in a test assay according to some embodiments of the present invention. In some embodiments, an intensity of 1.25 correlates with a concentration of lysozyme of 40 µg/ml observed in a test assay according to some embodiments of the present invention. In some embodiments, an intensity of 1.5 correlates with a concentration of lysozyme of 70 µg/ml observed in a test assay according to some embodiments of the present invention. In some embodiments, an intensity of 1.75 correlates with a concentration of lysozyme of 100 µg/ml observed in a test assay according to some embodiments of the present invention. In some embodiments, an intensity of 2.0 correlates with a concentration of lysozyme of 150 µg/ml observed in a test assay according to some embodiments of the present invention.

In some embodiments, the correlation of the test line indicates that a lower amount of lysozyme on a test assay according to some embodiments of the present invention, such as, for example, 0 to 1 µg/ml correlates with a lower result as detected by at least one test selected from the group consisting of the Schirmer's test, the corneal staining test, ODSI, and TFBUT.

In some embodiments, the correlation of the test line indicates that a lower amount of lysozyme on a test assay according to some embodiments of the present invention, such as, for example, 0 to 1 µg/ml correlates with a higher result as detected by at least one test selected from the group consisting of the Schirmer's test, the corneal staining test, ODSI, and TFBUT.

Measurement of Mucin in Tear Fluid Samples According to Some Embodiments of the Present Invention:

In some embodiments, the present invention is a method for quantifying an amount of mucin in a tear sample, comprising: collecting the tear sample containing the amount of mucin from a subject, and where the amount of mucin of the tear sample is used to generate a semi-quantitative intensity measurement of mucin by: collecting the tear sample containing the amount of mucin from the subject; contacting the tear sample containing the amount of mucin from the subject with a tear analyzing strip, where the tear analyzing strip is bound to an amount of Jacalin bound to biotin and an amount of wheat germ agglutinin (WGA), wherein the amount of the Jacalin bound to biotin is conjugated to colloidal gold at a ratio of 2.5 µg/ml to 10 µg/ml per 1 optical density (OD) per milliliter colloidal gold, incubating the amount of mucin from the subject on the tear analyzing strip so as to result in a line intensity of mucin; and utilizing the line intensity of mucin to determine the semi-quantitative intensity measurement of mucin; wherein the semi-quantitative intensity measurement of mucin is selected from the group consisting of: 0.25, 0.5, 0.75, 1.0, 1.25, 1.5, 1.75, and 2.0.

In some embodiments, the ratio is 2.5 µg/ml Jacalin bound to biotin per 1 OD per milliliter colloidal gold bound to streptavidin. In some embodiments, the ratio is 3 µg/ml Jacalin bound to biotin per 1 OD per milliliter colloidal gold bound to streptavidin. In some embodiments, the ratio is 3.5 µg/ml Jacalin bound to biotin per 1 OD per milliliter colloidal gold bound to streptavidin. In some embodiments, the ratio is 4 µg/ml Jacalin bound to biotin per 1 OD per milliliter colloidal gold bound to streptavidin. In some embodiments, the ratio is 4.5 µg/ml Jacalin bound to biotin per 1 OD per milliliter colloidal gold bound to streptavidin. In some embodiments, the ratio is 5 µg/ml Jacalin bound to biotin per 1 OD per milliliter colloidal gold bound to streptavidin. In some embodiments, the ratio is 5.5 µg/ml Jacalin bound to biotin per 1 OD per milliliter colloidal gold bound to streptavidin. In some embodiments, the ratio is 6 µg/ml Jacalin bound to biotin per 1 OD per milliliter colloidal gold bound to streptavidin. In some embodiments, the ratio is 6.5 µg/ml Jacalin bound to biotin per 1 OD per milliliter colloidal gold bound to streptavidin. In some embodiments, the ratio is 7 µg/ml Jacalin bound to biotin per 1 OD per milliliter colloidal gold bound to streptavidin. In some embodiments, the ratio is 7.5 µg/ml Jacalin bound to biotin per 1 OD per milliliter colloidal gold bound to streptavidin. In some embodiments, the ratio is 8 µg/ml Jacalin bound to biotin per 1 OD per milliliter colloidal gold bound to streptavidin. In some embodiments, the ratio is 8.5 µg/ml Jacalin bound to biotin per 1 OD per milliliter colloidal gold bound to streptavidin. In some embodiments, the ratio is 9 µg/ml Jacalin bound to biotin per 1 OD per milliliter colloidal gold bound to streptavidin. In some embodiments, the ratio is 9.5 µg/ml Jacalin bound to biotin per 1 OD per milliliter colloidal gold bound to streptavidin. In some embodiments, the ratio is 10 µg/ml Jacalin bound to biotin per 1 OD per milliliter colloidal gold bound to streptavidin.

Figure 5:
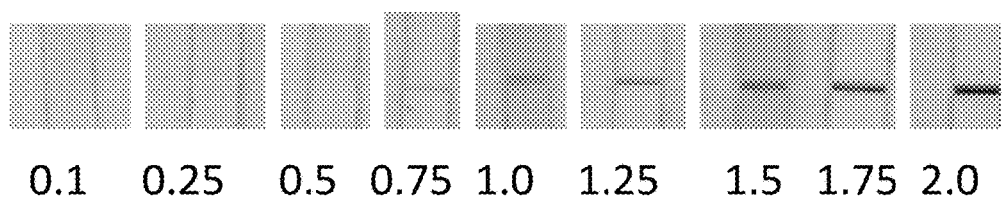
FIG. 5 shows the correlation of test line intensity obtained using a mucin assay according to some embodiments of the present invention with analyte concentration.

FIG. 5 illustrates the correlation of test line intensity obtained using a mucin assay according to some embodiments of the present invention with analyte concentration. In some embodiments, a reduced test line intensity correlates with an existing test for dry eye (e.g., Schirmer's test, corneal staining, OSDI, etc.).

Referring to FIG. 5, in some embodiments, an intensity of 0.1 correlates with a concentration of mucin of 0 µg/ml observed in a test assay according to some embodiments of the present invention. In some embodiments, an intensity of 0.25 correlates with a concentration of mucin of 0.1 µg/ml observed in a test assay according to some embodiments of the present invention. In some embodiments, an intensity of 0.5 correlates with a concentration of mucin of 0.5 µg/ml observed in a test assay according to some embodiments of the present invention. In some embodiments, an intensity of 0.75 correlates with a concentration of mucin of 1 µg/ml observed in a test assay according to some embodiments of the present invention. In some embodiments, an intensity of 1.0 correlates with a concentration of mucin of 3 µg/ml observed in a test assay according to some embodiments of the present invention. In some embodiments, an intensity of 1.25 correlates with a concentration of mucin of 6 µg/ml observed in a test assay according to some embodiments of the present invention. In some embodiments, an intensity of 1.5 correlates with a concentration of mucin of 12 µg/ml observed in a test assay according to some embodiments of the present invention. In some embodiments, an intensity of 1.75 correlates with a concentration of mucin of 25 µg/ml observed in a test assay according to some embodiments of the present invention. In some embodiments, an intensity of 2.0 correlates with a concentration of mucin of 50 µg/ml observed in a test assay according to some embodiments of the present invention.

In some embodiments, the correlation of the test line indicates that a lower amount of mucin on a test assay according to some embodiments of the present invention, such as, for example, 0 to 1 µg/ml correlates with a lower result as detected by at least one test selected from the group consisting of the Schirmer's test, the corneal staining test, ODSI, and TFBUT.

In some embodiments, the correlation of the test line indicates that a lower amount of mucin on a test assay according to some embodiments of the present invention, such as, for example, 0 to 1 µg/ml correlates with a higher result as detected by at least one test selected from the group consisting of the Schirmer's test, the corneal staining test, ODSI, and TFBUT.

Devices According to Some Embodiments of the Present Invention

In some embodiments, the present invention provides a device for determining the level of at least one tear constituent selected from the group consisting of: human serum albumin, lactoferrin, lysozyme, and mucin, the device comprising:
  a. a test strip configured to receive a tear sample from the patient; and
  b. a reagent pad, containing reagents specific for human serum albumin, that, upon contact with the tear sample, undergo a reaction configured to produce a color, wherein the intensity of the color is proportional to the amount of human serum albumin in the tear sample, and wherein the test strip is configured to deliver the tear sample to the reagent pad.

In some embodiments, the present invention provides a device for determining the level of at least one tear constituent selected from the group consisting of: human serum albumin, lactoferrin, and lysozyme, the device comprising:
  a. a test strip configured to receive a tear sample from the patient; and
  b. a plurality of reagent pads, wherein a first individual reagent pad contains reagents specific for human serum albumin, a second reagent pad contains reagents specific for lysozyme, and a third reagent pad contains reagents specific for lactoferrin, wherein the reagents in the first, second and third reagent pads, upon contact with the tear sample, undergo a reaction configured to produce a color, wherein the intensity of the color is proportional to the amount of the human serum albumin, lysozyme, and lactoferrin present in the tear sample, and wherein the test strip is configured to deliver the tear sample to the plurality of reagent pads.

In some embodiments, the reaction configured to produce a color is an immune-chemical reaction. In some embodiments, the reaction configured to produce a color is a binding reaction.

Figure 6:
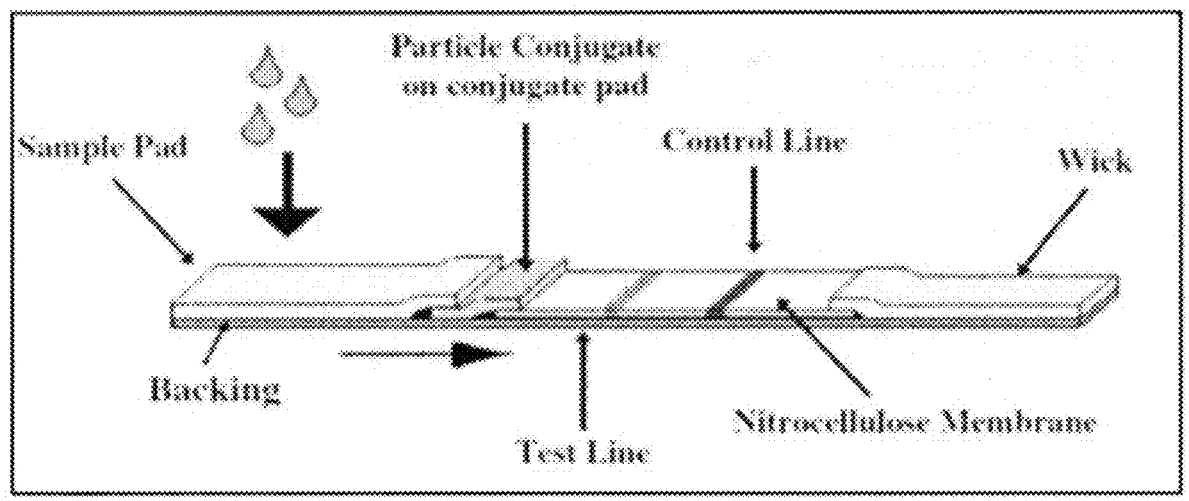
FIG. 6 shows a device according to some embodiments of the present invention.

FIG. 6 shows a non-limiting exemplary embodiment of a device according to some embodiments of the present invention. The device comprises one or more pads containing chemical or biological reagents which, upon contact with tears, undergo an immuno-chemical recognition with the tested analyte and migration of the complex to a defined zone. As a result of which, a colored line is observed. The diagnosis may be made after a predefined time, e.g. after completion of the immuno-chemical reaction. The diagnosis is based on comparing the color intensity of the observed line on the device reaction zone to a reference printed picture color line intensity. The printed picture of color line intensities wherein each of the color intensity represent one or more characteristics for diagnosing DES. Such characteristics may be, but not limited to, (a) the concentration of at least one substance the concentration of which is known to correlate with DES (a non-limiting example includes lysozyme), the concentration of at least one predefined protein level and electrolyte (such as sodium, potassium etc) (b) osmolarity, (c) viscosity and surface tension and (d) pH.

In some embodiments of the method of the present invention, the device can also be used to collect an amount of tear fluid sufficient for performing a medical diagnosis based on the relevant characteristics of the tears. In some embodiments, the device thus can provide qualitative, quantitative (e.g., but not limited to, using a strip reader), semi-quantitative and multi-factorial diagnosis. In some embodiments, the device thus can provide a semi-quantitative diagnosis.

In some embodiments, the method of the present invention includes providing two lectins, e.g., Pisum stivum agglutinin ("PSA") and Lens culinaris agglutinin ("LCA") [both manufactured by Medicago AB in: Danmark Berga 13, SE-755 98 Uppsala, Sweden or by VECTOR LABORATORIES, INC: 30 Ingold Road, Burlingame, Calif. 94010, USA], where PSA is conjugated to gold particles. In some embodiments, biotin is bound to PSA which generates biotin-PSA, and biotin-PSA is bound to streptavidin-gold conjugate. In some embodiments, the lectins are placed on a test strip. In some embodiments, at least one lectin is conjugated to gold particles ("immunogold labeled"). In some embodiments, the gold particles are colloidal gold particles. In some embodiments, the colloidal gold particles can range from 20-125 nm. In some embodiments, the colloidal gold particles can range from 50-125 nm. In some embodiments, the colloidal gold particles can range from 100-125 nm. In some embodiments, the colloidal gold particles can range from 20-100 nm. In some embodiments, the colloidal gold particles can range from 20-50 nm. In some embodiments, the colloidal gold particles can range from 20-40 nm. In some embodiments, the colloidal gold particles can range from 20-60 nm. In some embodiments, the colloidal gold particles can range from 40-60 nm. In some embodiments, the colloidal gold particles can range from 50-100 nm.

In some embodiments, the method of the present invention includes providing a lysozyme antibody (anti-lysozyme), where the anti-lysozyme is conjugated. In some embodiments, the anti-lysozyme antibody is placed on a test strip. In some embodiments, the anti-lysozyme antibody is obtained from a sheep (i.e., sheep anti-lysozyme and/or rabbit anti-lysozyme; where the sheep anti-Lysozyme may be supplied by Seramun GmbH [Spreenhagener Str. Heidesee 115754, GERMANY] or rabbit anti-Lysozyme supplied by Nordic MUbio [Rangeerweg 5A 6114 BC Susteren The Netherlands]). In some embodiments, the anti-lysozyme antibody is conjugated to gold particles ("immunogold labeled"). In some embodiments, the anti-sheep antibody is conjugated to gold particles (4 ug of antibodies to 1 ml of OD 1 40 nm gold particals). In some embodiments, the gold particles are colloidal gold particles. In some embodiments, the colloidal gold particles can range from 20-125 nm. In some embodiments, the colloidal gold particles can range from 50-125 nm. In some embodiments, the colloidal gold particles can range from 100-125 nm. In some embodiments, the colloidal gold particles can range from 20-100 nm. In some embodiments, the colloidal gold particles can range from 20-50 nm. In some embodiments, the colloidal gold particles can range from 50-100 nm. In some embodiments, the colloidal gold particles can range from 20-60 nm. In some embodiments, the colloidal gold particles can range from 40-60 nm. In some embodiments, the colloidal gold particles can range from 20-40 nm.

In some embodiments, the method of the present invention includes providing two lectins, e.g., pisum stivum agglutinin ("PSA") and lens culinaris agglutinin ("LCA"), where PSA is conjugated to gold particles. In some embodiments, biotin is bound to PSA which generates biotin-PSA, and biotin-PSA is bound to streptavidin-gold conjugate. In some embodiments, the lectins are placed on a test strip. In some embodiments, at least one lectin is conjugated to gold particles ("immunogold labeled"). In some embodiments, the gold particles are colloidal gold particles. In some embodiments, the colloidal gold particles can range from 20-125 nm. In some embodiments, the colloidal gold particles can range from 50-125 nm. In some embodiments, the colloidal gold particles can range from 100-125 nm. In some embodiments, the colloidal gold particles can range from 20-100 nm. In some embodiments, the colloidal gold particles can range from 20-50 nm. In some embodiments, the colloidal gold particles can range from 20-60 nm. In some embodiments, the colloidal gold particles can range from 20-40 nm. In some embodiments, the colloidal gold particles can range from 40-60 nm. In some embodiments, the colloidal gold particles can range from 50-100 nm.

In some embodiments, the test strip contains Nitrocellulose (e.g., but not limited to, Whatman's FF120 or the CNPH-N-SS60 from Advanced Microdevices PVT).

In some embodiments, the test strip includes free [i.e., unconjugated] sheep anti-lysozyme antibodies, where these free antibodies can control test sensitivity.

In some embodiments, the method of the present invention includes a comparative step where the semi-quantitative intensity measurement of lysozyme is correlated with results of the Schirmer's method. According to Schirmer's method, a paper strip is used to measure the amount of tears produced over a period of five minutes. The strip is placed at the junction of the middle and lateral thirds of the lower eyelid, between the eyeball and the lid. The test is done under ambient light. The patient is instructed to look forward and to blink normally during the course of the test. Wetting of more than 10 mm of the paper in 5 minutes is taken to indicate that the eye produces normal quantity of tears. The specificity (i.e., the ability of the test to identify normal individuals) of Schirmer method is usually around 90%. The Schirmer test provides true identification of DED suspected individuals—at a rate of 20% of total DED suspected population. The Schirmer test provides true positive results when the wetting is less the 5 mm and true negative results when the level of wetting is above 10 mm and may provide false positive results when the level of wetting is between 5 mm and 10 mm. When the level of wetting is between 5 mm and 10 mm the patient is suspected to have DES, but the results cannot be considered conclusive.

In some embodiments, the method of the present invention includes a comparative step where the semi-quantitative intensity measurement of lactoferrin is correlated with results of the Schirmer's method. According to Schirmer's method, a paper strip is used to measure the amount of tears produced over a period of five minutes. The strip is placed at the junction of the middle and lateral thirds of the lower eyelid, between the eyeball and the lid. The test is done under ambient light. The patient is instructed to look forward and to blink normally during the course of the test. Wetting of more than 10 mm of the paper in 5 minutes is taken to indicate that the eye produces normal quantity of tears. The specificity (the ability of the test to identify normal individuals) of Schirmer method is usually around 90%. The Schirmer test provides true identification of DED suspected individuals at a rate of 20% of total DED suspected population. The Schirmer test provides true positive results when the wetting is less the 5 mm and true negative results when the level of wetting is above 10 mm and may provide false positive results when the level of wetting is between 5 mm and 10 mm. When the level of wetting is between 5 mm and 10 mm the patient is suspected to have DES, but the results cannot be considered conclusive.

In some embodiments, the method of the present invention includes a comparative step where the semi-quantitative intensity measurement of mucin is correlated with results of the Schirmer's method. According to Schirmer's method, a paper strip is used to measure the amount of tears produced over a period of five minutes. The strip is placed at the junction of the middle and lateral thirds of the lower eyelid, between the eyeball and the lid. The test is done under ambient light. The patient is instructed to look forward and to blink normally during the course of the test. Wetting of more than 10 mm of the paper in 5 minutes is taken to indicate that the eye produces normal quantity of tears. The specificity (the ability of the test to identify negative results) of Schirmer method is usually around 90%. The Schirmer test provides true positive results when the wetting is less the 5 mm and true negative results when the level of wetting is above 10 mm and may provide false positive results when the level of wetting is between 5 mm and 10 mm. When the level of wetting is between 5 mm and 10 mm the patient is suspected to have DES, but the results cannot be considered conclusive.

Reference is now made to the following examples, which together with the above descriptions illustrate some embodiments of the invention in a non-limiting fashion.

EXAMPLES

Example 1: Measurement of Lactoferrin in Tear Samples According to Some Embodiments of the Present Invention The levels of a prominent tear constituent were examined in healthy subjects and in subjects who met one or more criteria of mild to moderate dry eye. The following experiments illustrate a comparison between benchmark testing for assessment of dry eye with a quantitative measure of a tear constituent. Examples of the tests used to quantitatively measure at least one tear constituent are corneal staining, Schirmer's tests, TFBUT, and provided symptom assessment including the OSDI questionnaire and the Ora-Calibra™ ocular discomfort score. The OSDI is a 12 questions assessment that has become a standard for dry eye symptomology. The Ora-Calibra™ assessments for discomfort also provide a measurement of symptomology by allowing a patient to answer questions, where the number of questions is reduced compared to the OSDI. Samples of tears were collected using capillary tubes and then underwent analysis for the tear constituent. The tear constituent measured was lactoferrin.

Tear Constituent Assay and Measurement Methodology

Rapid test strips (tear analyzing strips) and reagents were used to measure lactoferrin levels using a semi-quantitative technique; where the semi-quantitative technique followed a fixed running time for each type of assay, strips were scanned with HP's scanner model scanjet 200. The scanned figure was optimized using Function Lighten/Darken: Highlights—(−) 50; Shadows—(−) 69; Midtones—(−) 50; Gamma—1.7 followed by recording of signal intensity (shown in FIG. 2). Determination of the tear constituent was conducted using semi-quantitative estimation of the intensity test lines compared to intensity of a series of control lines.

Experimental Design

Subject Population: Subjects for the study included anyone over the age of 18 years who met the inclusion and exclusion criteria listed in the following tables. The study population included two groups of subjects (Group A, as shown in Table 1, and Group B, shown in Table 2) with approximately equal numbers of each (approximately 100 subjects per group):

TABLE 1

Group A - Healthy Eyes

Healthy Subjects, Inclusion Criteria

1. Subject must be 18 years of age and may be of any race and either gender;
2. The IRB approved informed consent must be read, signed, and dated by the subject or legally authorized representative. Additionally, the informed consent must be signed and dated by the individual consenting the subject;
3. Subject agrees for samples to be taken from both eyes;
4. Subject must be willing to follow the study procedures and visit schedule;
5. Subject must report <2 in all symptoms (Ora Calibra ™ Ocular Discomfort & 4- Symptom Questionnaire) during visit;
6. Subject has at least one of the following in the collection eye(s):
a. <2 in all regions of the cornea (Ora Calibra ™ Scale) during visit;
b. TFBUT > 10 seconds during visit.

Healthy Subjects, Exclusion Criteria

1. Subject complained of dry eye or any other acute ocular disease;
2. Subject is currently suffering from active inflammation or infection;
3. Subject used artificial tear drops in the past 2 months;
4. Subject currently treated medically for a chronic eye syndrome such as glaucoma, allergy or conjunctivitis;
5. Subject has a condition, which in the opinion of the Principal Investigator, would interfere with optimal participation in the study, or which would present a special risk to the subject;
6. Subject reports currently being pregnant or nursing;
7. Use of investigational study drug or study device within 30 days of enrollment.

TABLE 2

Group B - Suspected Dry Eye

Suspected Dry Eye, Inclusion Criteria

1. Subject must be 18 years of age and may be of any race and either gender;
2. The IRB approved informed consent must be read, signed, and dated by the subject or legally authorized representative. Additionally, the informed consent must be signed and dated by the individual consenting the subject;
3. Subject used or had the desire to use artificial tears in the last 30 days;
4. Subject reports ≥2 in at least one symptom (Ora CalibraTM Ocular Discomfort & 4- Symptom Questionnaire) during visit;
5. Subject demonstrates both of the following in the collection eye(s):
a. ≥2 in at least one region (Ora Calibra ™ scale)
b. TFBUT < 10 seconds during visit;
6. Subject agrees for samples to be taken from both eyes;
7. Subject must be willing to follow the study procedures and visit schedule.

Suspected Dry Eye, Exclusion Criteria

1. Subject is using contact lenses on a regular basis;
2. Subject is currently suffering from active inflammation or infection;
3. Subject has used Restasis ® in the last 30 days;
4. Subject used artificial tear drops in the past hour;
5. Subject is being medically treated for glaucoma;
6. Subject has a condition, which in the opinion of the Principal Investigator, would interfere with optimal participation in the study, or would present a special risk to the subject;
7. Subject reports currently being pregnant or nursing;
8. Subject has participated in any other clinical trial within 30 days of enrollment.

An exemplary embodiment of the method of the present invention was a prospective, single-center, single-visit, parallel-group, data and tear collection study, consisting of approximately 200 subjects. There was one scheduled study visit where subjects were screened; those who met the eligibility criteria were enrolled in the study.

Tear Sample Collection:

The procedure for tear sample collection was as follows:
1. The slit-lamp was set at a low intensity beam.
2. The lower lid of the eye was retracted and a glass capillary tube was placed on the temporal aspect touching the tear surface.
3. The tear surface was contacted and allowed for the collection of between 6-25 microliters of tear solution.
4. Once a sufficient volume (e.g., but not limited to, 6-25 microliters) was collected, the contents of the glass capillary was withdrawn and emptied into a vial. If tear volume was below 6 microliters, a second sample was drawn from the other eye into another clean vial.
5. The vials were marked with a designated subject label provided by the sponsor.
6. The vials were stored at a temperature of 2° c.-8° c. Tear samples were transferred to the sponsor laboratories for initial preparation up to 48 hours from collection before further analysis for levels of lactoferrin.
7. The tear volume was measured within the 48 hours from sampling using pipette of small volume. Two sample volumes of Phosphate buffer saline (PBS×1) were added to collected sample followed by a short vortex (20 Sec.) for mixing. Diluted samples were placed back for storage in a temperature of 2° C.-8° C.

Lactoferrin Assay:

The assay allows for direct detection of the lactoferrin in human tears using specific detection of sugar groups of lactoferrin (i.e. a glycoprotein) using a Lateral Flow immunochromatographic assay. First, 20 µl of tear sample diluted 1:2000 was placed on the sample pad. Then, additional 40 µl of washing solution were placed on the sample pad to allow the tear sample to migrate and wet the conjugate pad. The conjugate pad contained a first lectin (e.g., pisum stivum agglutinin ("PSA")) conjugated to streptavidin conjugated to gold particles (manufactured by Arista Biologicals Inc. 1101 Hamilton Street, Allentown, Pa. 18101) through biotin avidin interaction. The conjugated lectin bound the lactoferrin from the tear sample and migrated through the nitrocellulose membrane towards the wick. When the gold conjugate/lactoferrin complexes reached the test zone, the gold conjugate/lactoferrin bound to the second lectin (e.g., lens culinaris agglutinin ("LCA")) fixated to the membrane surface (i.e., at the test line). The accumulation of the gold conjugate/lactoferrin bound to the test line form a pinkish red visible line. An excess amount of complex then migrated to a second zone containing biotin BSA that bounds the streptavidin gold conjugate. A second line is formed (a control line). The control line indicated test validity. A residual amount of conjugate and tear sample migrated from the nitrocellulose membrane into the wick pad.

The test strip was produced as follows: 1 mg/ml (0.75-1.5 mg/ml) LCA was impregnated onto a chromatographic membrane of nitrocellulose (e.g., Whatman's nitrocellulose membrane, FF120 but can also be mdi CNPH-N-5560 membrane). LCA was impregnated on the test strip in the shape of a 1 mm wide line. The LCA solution additionally contains the following: (1) buffer, e.g., phosphate buffered saline at pH 7.4 or Tris, HEPES, Borax, or MES buffer with pH value ranging from 6.5-9.0; (2) 2% trehalose or sucrose, ranging from 1%-4% concentration; (3) 1-4% ethanol (e.g., but not limited to, 1%, 2%, 3%, 4% ethanol). The LCA impregnated nitrocellulose was dried at 50 degrees C. for 10 minutes to bind the protein to the nitrocellulose. Binding of the LCA to nitrocellulose can also occur between 37-60 degrees C. for 5 to 24 hours, where a higher temperature would allow for a shorter incubation time. The biotin was bound to PSA by conjugating biotin to PSA at a ratio of, e.g., but not limited to, 11:1, 22:1, or 33:1. Biotin-PSA was bond to streptavidin-gold conjugate at a ratio of 5 ug/ml biotin-PSA (but can range from 1 ug/ml to 7 μg/ml of concentration) and between OD0.5/ml-OD2.0/ml, e.g., but not limited to, OD1/ml, gold-streptavidin. The reaction complex can also include wash reagent, which clears excess gold conjugates from the nitrocellulose membrane. The wash reagent can contain the following: (1) PBS×1 at pH 7.4 (can range from pH 7.0-9.0); (2) 1% fatty-acid free bovine serum albumin (can range from 0.5%-3.0%); (3) 0.1% Tween 20 (can range from 0.05%-2.0%); (4) 0.05% sodium dodecylsulfate (can range from 0.01%-1%), or any combination thereof. Regarding FIG. 1, the line intensity of 1 is formed when lactoferrin is measured at 50 μg/mL (i.e., showing equivalence between line intensity and lactoferrin concentration).

Tear Film Break Up Time Test:
The procedure for TFBUT included:
1. A medical professional instilled 5 μL of 2% preservative-free sodium fluorescein solution into the inferior conjunctival cul-de-sac of each eye. To thoroughly mix the fluorescein with the tear film, the subject was instructed to blink several times. In order to achieve maximum fluorescence, the medical professional waited approximately 30 seconds after instillation before evaluating TFBUT.
2. With the aid of a slit lamp, the medical professional monitored the integrity of the tear film, noting the time it takes to form micelles from the time that the eye was opened. TFBUT was measured in seconds using a stopwatch and a digital image recording system for the right eye followed by the left eye. A Wratten #12 yellow filter was used to enhance the ability to grade TFBUT.
3. For each eye, two measurements were taken and averaged unless the two measurements were greater than 2 seconds apart and were each less than 10 seconds, in which case, a third measurement was taken and the two closest of the three was averaged.

Corneal Fluorescein Staining:
The procedure for corneal fluorescein included:
1. In order to achieve maximum fluorescence, the medical professional waited approximately 3-5 minutes after instillation before evaluating fluorescein staining. A Wratten #12 yellow filter was used to enhance the ability to grade fluorescein staining.
2. The inter-palpebral was graded and recorded, and the conjunctiva and cornea epithelial were stained by use of a 5 point scale (e.g., pictures of scanned strips/panel which had line intensity representing one degree of the intensities scale). The upper eyelid was lifted slightly to grade the whole corneal surface. Regarding conjunctiva, temporal zone grading was performed when the subject looks nasally; grading nasally by looking temporally.
3. The conjunctival and corneal staining was graded and recorded using the Ora Calibra™ Corneal and Conjunctival Staining Scale.

Unanesthetized Schirmer's Test:
The Schirmer Tear Test was performed according to the following procedure:
1. Using a sterile Tear Flo Schirmer's test strip (e.g., obtained from, but not limited to, Rose Enterprises), a bend in the strip was made in line with the notch in the strip.
2. The subject was instructed to gaze up and in.
3. The Schirmer's test strip was placed in the lower temporal lid margin of each eye such that the strip fits tightly. Subjects were instructed to close their eyes.
4. After 5 minutes have elapsed, the Schirmer's strip was removed. The length of the moistened area was recorded (mm) for each eye.

Ora Calibra™ Ocular Discomfort Scale:
In an exemplary embodiment, ocular discomfort scores were subjectively graded by the subjects according to the following scale, rating each eye separately. The scale used is shown below and ranges from 0-4:
0=no discomfort
1=intermittent awareness
2=constant awareness
3=intermittent discomfort
4=constant discomfort Ora Calibra™ Ocular Discomfort & 4-Symptom Questionnaire:
Subjects rated the severity of each of the following symptoms, with regards to how both their eyes felt, in general—overall ocular discomfort, burning, dryness, grittiness and stinging according to the following 6-point (0 to 5) scale where 0=none and 5=most.

| 0 (None) | 1 | 2 | 3 | 4 | 5 (Most) |
|---|---|---|---|---|---|

Standards of professional care to protect the ocular safety of subjects were followed with regard to study regimen adherence. Subjects who met entry criteria provided demographic information, medical and ocular history and artificial tears use if appropriate. Clinical staff confirmed that subjects did not use artificial tears in the hour prior to the study, then guided subjects through the following procedures:
1. Subjects completed the OSDI© questionnaire and Ora Calibra™ Ocular Discomfort & 4-symptom Questionnaire.
2. Subjects and staff reviewed source documents to confirm that subject met all inclusion/exclusion criteria based on current medications and medical history.
3. Clinical staff collected 6-25 microliters of tears using a capillary from the right eye of the subject. Staff labeled the collection vial with the subject screening number and emptied the capillary contents into the vial.
4. In the cases where tear volume collected from the right eye was below 6 microliters, a sample was drawn from the left eye and the capillary was emptied into another clean vial marked with same subject screening number.
5. Clinical staff performed tear film break up time test on collection eye(s).
6. Clinical staff performed Corneal Fluorescein Staining and examined the ocular surface of the collection eye(s).
7. If 6 or greater microliters were collected from the right eye, but the subject did not meet Tear Film Break Up Time or Fluorescein Staining inclusion criteria in the right eye, steps 3-6 were repeated in left eye.
8. Clinical staff performed un-anesthetized Schirmer's Test on collection eye(s).
9. Clinical staff reviewed results to determine if patient met all inclusion/exclusion criteria based on data collected according to items 3-8.
10. Patients who met all criteria were assigned a subject study number and categorized on label based on diagnosis of healthy or suspected dry eye patient.
11. Adverse events, if applicable, were documented.

Samples were handled and tested using the following parameters:
1. Volume of collected tears was measured using a micropipette. Twice the measured volume was added with Phosphate Buffer Saline (PBS) for a final dilution of 1:3.
2. Diluted tears were further diluted serially to the following dilutions: 1:50, 1:100 and 1:200 with PBS.
3. Two microliters of diluted sample were mixed with 18 microliters of gold conjugate mix in a microtube. The relevant test strip was dipped in that mix for 4 minutes.
4. Additional 25 microliters of wash solution were added to the tube for excess dye clearance from reaction zone.
5. After 6 minutes developed test strips were gently blot against tissue paper and scanned with a desk scanner.
6. Test intensity was quantified according to the intensity scale presented in FIG. 2.

Power Analysis:
Table 3 presents power for selected sample sizes.

TABLE 3

| Performance Goal | Sample Proportion | N | Power |
|---|---|---|---|
| 0.55 | 0.70 | 95 | 0.82 |
| | 0.72 | 75 | 0.82 |
| | 0.75 | 50 | 0.84 |
| 0.60 | 0.70 | 100 | 0.55 |
| | 0.72 | 100 | 0.71 |
| | 0.75 | 90 | 0.84 |

TABLE 3-continued

| Performance Goal | Sample Proportion | N | Power |
|---|---|---|---|
| 0.65 | 0.70 | 100 | 0.16 |
| | 0.72 | 100 | 0.29 |
| | 0.75 | 100 | 0.55 |

The power was estimated using Exact Binomial method, where two co-primary endpoints (sensitivity and specificity) were taken into account, and where "N" represents the number of positive only (or negative only) cases. Thus, the total sample size was doubled.

Table 4 illustrates a "Precision" parameter, which is defined as a half-length of confidence interval (CI). The CI is an interval estimate of a population parameter. The CI is an observed interval (i.e. it is calculated from the observations), in principle different from sample to sample, that frequently includes the parameter of interest if the experiment is repeated.

TABLE 4

| Sample Size | Obtained Number of Responders | Obtained Rate | 95% Lower CI | 95% Upper CI | Precision |
|---|---|---|---|---|---|
| 80 | 48 | 60.0% | 48.4% | 70.8% | 11.2% |
| | 52 | 65.0% | 53.5% | 75.4% | 11.0% |
| | 56 | 70.0% | 58.7% | 79.8% | 10.6% |
| | 60 | 75.0% | 64.0% | 84.1% | 10.1% |
| | 64 | 80.0% | 69.5% | 88.2% | 9.4% |
| | 68 | 85.0% | 75.2% | 92.1% | 8.5% |
| | 72 | 90.0% | 81.2% | 95.6% | 7.2% |
| 90 | 54 | 60.0% | 49.1% | 70.2% | 10.6% |
| | 59 | 65.6% | 54.7% | 75.3% | 10.3% |
| | 63 | 70.0% | 59.4% | 79.3% | 10.0% |
| | 68 | 75.6% | 65.3% | 84.1% | 9.4% |
| | 72 | 80.0% | 70.2% | 87.7% | 8.8% |
| | 77 | 85.6% | 76.5% | 92.1% | 7.8% |
| | 81 | 90.0% | 81.8% | 95.4% | 6.8% |
| 100 | 60 | 60.0% | 49.7% | 69.7% | 10.0% |
| | 65 | 65.0% | 54.8% | 74.3% | 9.8% |
| | 70 | 70.0% | 60.0% | 78.8% | 9.4% |
| | 75 | 75.0% | 65.3% | 83.2% | 9.0% |
| | 80 | 80.0% | 70.8% | 87.4% | 8.3% |
| | 85 | 85.0% | 76.4% | 91.4% | 7.5% |
| | 90 | 90.0% | 82.3% | 95.1% | 6.4% |

Results and Analysis

The primary outcome of the study was the comparison of benchmark tests for dry eye such as TFBUT, Corneal staining, Schirmer's test, and OSDI questionnaires with results from a test of tear film constituents (e.g., lactoferrin).

All collected samples obtained from patients' eyes which met the entry criteria were included in the analyses. The goal of the study was to develop an assessment tool to compare benchmark tests for dry eye with a kit that tests the tear film compound, lactoferrin. Data was distributed from lowest to highest values and compared with other parameters to identify positive and negative correlations. FIG. 2 illustrates the correlation of test line intensity with analyte concentration. In some embodiments, a reduced test line intensity correlates with a test for dry eye (e.g., Schirmer's test, corneal staining, OSDI, etc.).

In some embodiments, the correlation of the test line indicates that a lower amount of lactoferrin on a test assay according to some embodiments of the present invention, such as, for example, 1 to 4 μg/ml correlates with a higher result as detected by at least one test selected from the group consisting of the Schirmer's test, the corneal staining test, ODSI, and TFBUT.

Sample size in this pilot study (198 total eyes, 99 per group) was not based on any power analysis, but was based on an approximation of the number of eyes sufficient to build a model for a distinguishing between healthy and suspected dry eye tears and evaluation of benchmark standard testing with the different tested parameters.

Adverse Events (AEs) included any events reported over the course of the tear collection and ocular surface assessment procedures. This clinical study involved TFBUT, corneal staining and the collection of tears for the constituent analysis. During these tests the participant may have felt a foreign body sensation. During the tear collection there may have been cases of direct contact with the eye due to movement, resulting in corneal abrasion, or eye redness. Any such events were noted and graded as follows:

Mild: Sign or symptom, usually transient, requiring no special treatment, generally not interfering with usual activities.

Moderate: Sign or symptom, which may be ameliorated by simple therapeutic measures; may interfere with usual activity.

Severe: Sign or symptom that are intense or debilitating and that interfere with usual activities. Recovery was usually aided by therapeutic measures.

A total of 198 subjects completed the study, including 126 women and 72 men. The breakdown of subjects according to entry criteria A or B is outlined in Table 5 below. Those who met entry criteria were not matched for age or gender in this study.

TABLE 5

|  | Men | Women | mean age |
|---|---|---|---|
| Group A Healthy | 41 | 59 | 45.5 |
| Group B Suspected DE | 31 | 67 | 58.6 |

Subjects enrolled in each study group met the entry criteria of either healthy or suspected dry eye. The only demographic criteria that showed a significant difference between the two groups was age; preliminary analysis showed no significant difference in any tear metrics between the two groups. In addition, both groups displayed a range of values for the benchmark testing parameters. Based upon this observation, all subjects were pooled into a single group and analyzed using population quartiles with an assumption that the population sampled represented a continuum of dry eye severity. Using this concept, measurements for each of the benchmark tests were ranked, and mean values for each of 4 quartiles were compared to measures for the tear diagnostics.

Quartile Analysis:

The quartile analysis for TFBUT, inferior staining, and Schirmer's tests are summarized in Table 6. The focus of this approach was on the extremes, quartiles 1 and 4, as these represent those patients with the largest differences for each metric. In all three measures, Q1 was the quartile with values expected for normal patients and Q4 was the quartile with values associated with dry eye disease. For example, those in Q1 have a mean TFBUT of 12.80 seconds and so would be considered normal while those in Q4 have a mean TFBUT of 2.34 seconds, consistent with a diagnosis of moderate dry eye disease. When the mean values for tested parameters in each of the TFBUT-defined quartiles were compared, associations between the break-up time metric and tear constituent dynamics emerged. The decrease in TFBUT between Q1 and Q4 was accompanied by an increase in lactoferrin. Inferior staining increases from Q1 to Q4, and this increase was significantly correlated with an increase in lactoferrin. Quartiles defined by Schirmer's scores exhibited significant negative correlations: while the mean Schirmer's score went down from Q1 to Q4, values for lactoferrin increases, and showed a significant difference between Q1 and Q4. This negative correlation was due to the nature of the Schirmer's scores, where higher values (Q1) indicated a healthy tear production.

Table 6 shows quartile analysis for TFBUT, inferior staining and Schirmer's Test. T-test values, where significant (less than 0.05), are highlighted in bold.

TABLE 6

| TFBUT | | | % of | Mean values |
|---|---|---|---|---|
| | Mean | n | eyes | Lactoferrin |
| Q1 | 12.80 | 48 | 24.6% | 0.979 |
| Q4 | 2.34 | 48 | 24.6% | 1.099 |
| Q4 − Q1 | −10.46 | | | 0.120 |
| Q1 vs. Q4, t test | | | | 0.037 |
| Inferior Staining | | | % of | |
| | Mean | n | eyes | Lactoferrin |
| Q1 | 0.42 | 52 | 27.5% | 0.596 |
| Q4 | 2.25 | 59 | 31.2% | 0.808 |
| Q4 − Q1 | 1.83 | | | 0.212 |
| Q1 vs. Q4, t test | | | | 0.003 |
| Schirmer's Test | | | % of | |
| | Mean | n | eyes | Lactoferrin |
| Q1 | 32.44 | 52 | 26.40% | 0.587 |
| Q4 | 5.21 | 52 | 26.40% | 0.803 |
| Q4 − Q1 | −27.23 | | | 0.216 |
| Q1 vs. Q4, t test | | | | >0.001 |

A second round of quartile analysis used the same approach to determine whether quartiles defined by tear constituent values show similar correlations with other metrics of the signs and symptoms of dry eye disease. These data are shown in Table 7. Table 7. Quartile analysis for lactoferrin. T-test values, where significant (<0.05), are highlighted in bold.

TABLE 7

| Lactoferrin Means | N | % of eyes | Mean Values |||||
|---|---|---|---|---|---|---|---|---|
| | | | TFBUT | OSDI | Ora Calibra Ocular Discomfort | Inferior | Corneal Sum | Schirmer's |
| Q1 0.42 | 90 | 45.45% | 6.19 | 13.66 | 1.12 | 1.14 | 2.66 | 19.22 |
| Q4 1.05 | 57 | 28.79% | 5.79 | 15.35 | 1.44 | 1.56 | 3.41 | 13.28 |
| Q1-Q4 | | | 0.40 | −1.69 | −0.32 | −0.42 | −0.76 | 5.94 |
| Q1 vs. Q4, t-test | | | 0.603 | 0.544 | 0.167 | 0.001 | 0.010 | 0.001 |

The quartiles associated with lacrimal gland protein lactoferrin displayed a significant difference for corneal staining measures, with inferior and total corneal staining showing a positive correlation with increases in protein levels from Q1 to Q4.

Discussion

The current study illustrated the heterogeneity of the two populations of subjects originally enrolled for analysis. Despite their inclusion based upon differential criteria for symptomology, TFBUT and corneal staining, no significant differences between the two populations were identified in the tear constituent analysis.

In some embodiments, the method of the present invention provides for a method of measuring dry eye, including tear constituent analysis. In some embodiments, the method of the present invention provides for a method of measuring dry eye, including tear constituent analysis, and comparing tear constituent analysis to tests such as, but not limited to, Schirmer's test, TFBUT, etc., so as to obtain information to treat a patient diagnosed with dry eye disease.

The quartile analyses show the relationships between traditional metrics and the tested parameters which are part of the tear constituents. An exception to this is TFBUT, which shows only modest correlations with any of the measured tear constituents. In contrast, corneal staining measures (such as inferior staining, Table 6) are well-correlated with changes in the tested parameters. This is consistent with a diagnosis of evaporative dry eye, where a reduction in aqueous content of the tears would yield apparent increases in the concentrations of all tear constituents. Alternatively, the increases in tear constituent concentration(s) can result from an inflammatory response to ocular surface distress that initiates a shift in the ratio of serious to mucus lacrimal secretions. Additionally, greater amounts of lactoferrin correlate with greater staining and lower Schirmer's scores; additionally, lactoferrin shows significant correlation with a lower TFBUT.

In some embodiments, the method of the present invention includes the use of at least one diagnostic test. In some embodiments, in performing such a comparison of tear constituents in healthy and dry eye subjects, a multiplicative effect is obtained. In some embodiments, a kit is used to provide an assessment between severe patients and healthy subjects.

Example 2: Measurement of Lysozyme in Tear Samples According to Some Embodiments of the Present Invention The levels of a prominent tear constituent were examined in healthy subjects and in subjects who met one or more criteria of mild to moderate dry eye. The following experiments illustrate a comparison between benchmark testing for assessment of dry eye with a quantitative measure of a tear constituent. Examples of the tests used to quantitatively measure at least one tear constituent are corneal staining, Schirmer's tests, TFBUT, and provided symptom assessment including the OSDI questionnaire and the Ora-Calibra™ ocular discomfort score. The OSDI is a 12 questions assessment that has become a standard for dry eye symptomology. The Ora-Calibra assessments for discomfort also provide a measurement of symptomology by allowing a patient to answer questions, where the number of questions is reduced compared to the OSDI. Samples of tears were collected using capillary tubes and then underwent analysis for the tear constituent. The tear constituent measured was lysozyme.

Tear Constituent Assay and Measurement Methodology

Rapid test strips (tear analyzing strips) and reagents were used to measure lactoferrin levels using a semi-quantitative technique; where the semi-quantitative technique followed a fixed running time for each type of assay, strips were scanned with HP's scanner model scanjet 200. The scanned figure was optimized using Function Lighten/Darken: Highlights—(−) 50; Shadows—(−) 69; Midtones—(−) 50; Gamma—1.7 followed by recording of signal intensity (shown in FIG. 4). Determination of the tear constituent was conducted using semi-quantitative estimation of the intensity test lines compared to intensity of a series of control lines.

Experimental Design

Subject Population: Subjects for the study included anyone over the age of 18 years who met the inclusion and exclusion criteria listed in the following tables. The study population included two groups of subjects (Group A, as shown in Table 1 in Example 1 above, and Group B, shown in Table 2 in Example 1 above) with approximately equal numbers of each (approximately 100 subjects per group):

An exemplary embodiment of the method of the present invention was a prospective, single-center, single-visit, parallel-group, data and tear collection study, consisting of approximately 200 subjects. There was one scheduled study visit where subjects were screened; those who met the eligibility criteria were enrolled in the study.

Tear Sample Collection:

The procedure for tear sample collection was according to the method described in Example 1 above.

Lysozyme Assay:

The assay allows for direct detection of the lysozyme in human tears using specific antibodies that recognize the enzyme. The test strip utilizes semi-quantitative lateral flow immunochromatographic technology. A tear sample is diluted 1:200 with phosphate saline buffer (i.e., further to the initial 1:3 dilution of the tear) 10 µl of sample diluted 1:200 are placed on the sample pad. Additional 40 μl washing solution allows the tear sample to migrate, wetting a conjugate pad. Specific sheep polyclonal antibodies conjugated to gold particles bind the lysozyme. The conjugated antibodies bound to the lysozyme flow through the nitrocellulose membrane. When the gold conjugate/lysozyme complex reaches the test zone, it reacts with secondary sheep anti-lysozyme antibodies fixated to the membrane surface. A second zone on the nitrocellulose is impregnated (e.g., with goat anti sheep antibodies) and is configured to bind the sheep anti-lysozyme-gold conjugate. A second line forms and is referred to as the Control Line. The control line indicates of test validity. Notably, the two anti-lysozyme antibodies (i.e., a sheep anti-lysozyme or a rabbit anti-lysozyme) can recognize different epitopes on the enzyme.

In an exemplary embodiment, 1.5 mg/ml (0.75-2.5 mg/ml) sheep anti lysozyme was impregnated onto a chromatographic membrane of nitrocellulose with high protein binding capacity (e.g., but not limited to, mdi CNPH-N-5560). Impregnation was visualized by, e.g., but not limited to, the naked eye, as a 1 mm wide line. The antibody solution contained the following: a. Buffer, for example, Phosphate buffer saline at pH 7.4 or Tris, HEPES, Borax or MES buffer with pH value ranging from 6.5 to 9.0; b. 2% Trehalose (can also be Sucrose), can also range between 1% to 4% sugar; c. 2% ethanol, can also range from 1 to 4%.

Antibody impregnated nitrocellulose was dried at 50° C. for 10 Min to allow the protein fixation to the nitrocellulose. In an embodiment, binding can occur between 60° C. and 37° C. for 5 to 24 hours, as modulated by temperature (e.g., faster binding at higher temperatures).

In an exemplary embodiment, sheep anti-lysozyme is conjugated to gold particles (e.g., 20 nm, 40, nm, 60 nm or 100 nm) at a ratio of 4 μg protein per OD1 per ml colloidal gold at 528 nm. Conjugation was performed under pH conditions of between pH 7 and pH 9, e.g., pH8.

An effective concentration of the gold conjugate can range from OD0.5/ml to OD 2/ml. 30 μg/ml of free sheep anti lysozyme (rabbit anti lysozyme can be used as well) was added to conjugate solution to adjust test sensitivity. Line intensity was estimated (i.e., semi-quantitatively measured) visually as shown in FIG. 4. A line intensity of 1 was formed when lysozyme was at a concentration of 25 μg/ml (showing, e.g., equivalence between line intensity and lysozyme concentration). The reaction mix also includes Wash Reagent (WR) that provides chemical surrounding as well as clearing of gold residuals from the nitrocellulose membrane. The WR contains the following: (a) PBS×1 pH 7.4 (can range from 7 to 9), (b) 1% Bovine Serum Albumin (BSA) can range from 0.5 to 3% and is fatty acid free), (c) between 0.05% and 2% Tween 20, e.g., but not limited to, 0.1% Tween 20, (d) 0.05% N-lauroyl sarcosine and 0.4% PEG to reduce non-specific binding to the nitrocellulose membrane, where the concentration of N-lauroyl sarcosine was from 0.01-1%.

Tear Film Break Up Time Test:

The procedure was carried out according to the method described in Example 1 above.

Corneal Fluorescein Staining:

The procedure was carried out according to the method described in Example 1 above.

Unanesthetized Schirmer's Test:

The procedure was carried out according to the method described in Example 1 above.

Ora Calibra™ Ocular Discomfort Scale:

The procedure was carried out according to the method described in Example 1 above.

Ora Calibra™ Ocular Discomfort & 4-Symptom Questionnaire:

The questionnaire was carried out according to the method described in Example 1 above.

Standards of professional care to protect the ocular safety of subjects were followed with regard to study regimen adherence. Subjects who met entry criteria provided demographic information, medical and ocular history and artificial tears use if appropriate. Clinical staff confirmed that subjects did not use artificial tears in the hour prior to the study, then guided subjects through the following procedures:

1. Subjects completed the OSDI© questionnaire and Ora Calibra™ Ocular Discomfort & 4-symptom Questionnaire.
2. Subjects and staff reviewed source documents to confirm that subject met all inclusion/exclusion criteria based on current medications and medical history.
3. Clinical staff collected 6-25 microliters of tears using a capillary from the right eye of the subject. Staff labeled the collection vial with the subject screening number and emptied the capillary contents into the vial.
4. In the cases where tear volume collected from the right eye was below 6 microliters, a sample was drawn from the left eye and the capillary was emptied into another clean vial marked with same subject screening number.
5. Clinical staff performed tear film break up time test on collection eye(s).
6. Clinical staff performed Corneal Fluorescein Staining and examined the ocular surface of the collection eye(s).
7. If 6 or greater microliters were collected from the right eye, but the subject did not meet Tear Film Break Up Time or Fluorescein Staining inclusion criteria in the right eye, steps 3-6 were repeated in left eye.
8. Clinical staff performed un-anesthetized Schirmer's Test on collection eye(s).
9. Clinical staff reviewed results to determine if patient met all inclusion/exclusion criteria based on data collected according to items 3-8.
10. Patients who met all criteria were assigned a subject study number and categorized on label based on diagnosis of healthy or suspected dry eye patient.
11. Adverse events, if applicable, were documented.

Samples were handled and tested using the following parameters:

1. Volume of collected tears was measured using a micropipette. Twice the measured volume was added with Phosphate Buffer Saline (PBS) for a final dilution of 1:3.
2. Diluted tears were further diluted serially to the following dilutions: 1:50, 1:100 and 1:200 with PBS.
3. Two microliters of diluted sample were mixed with 18 microliters of gold conjugate mix in a microtube. The relevant test strip was dipped in that mix for 4 minutes.
4. Additional 25 microliters of wash solution were added to the tube for excess dye clearance from reaction zone.
5. After 6 minutes developed test strips were gently blotted against tissue paper and scanned with a desk scanner.
6. Test intensity was quantified according to the intensity scale presented in FIG. 4.

Power Analysis:

Table 8 presents power for selected sample sizes.

TABLE 8

| Performance Goal | Sample Proportion | N | Power |
|---|---|---|---|
| 0.55 | 0.70 | 95 | 0.82 |
|  | 0.72 | 75 | 0.82 |
|  | 0.75 | 50 | 0.84 |
| 0.60 | 0.70 | 100 | 0.55 |
|  | 0.72 | 100 | 0.71 |
|  | 0.75 | 90 | 0.84 |
| 0.65 | 0.70 | 100 | 0.16 |
|  | 0.72 | 100 | 0.29 |
|  | 0.75 | 100 | 0.55 |

The power was estimated using Exact Binomial method, where two co-primary endpoints (sensitivity and specificity) were taken into account, and where "N" represents the number of positive only (or negative only) cases. Thus, the total sample size was doubled.

Table 9 illustrates a "Precision" parameter, which is defined as a half-length of confidence interval (CI). The CI is an interval estimate of a population parameter. The CI is an observed interval (i.e. it is calculated from the observations), in principle different from sample to sample, that frequently includes the parameter of interest if the experiment is repeated.

TABLE 9

| Sample Size | Obtained Number of Responders | Obtained Rate | 95% Lower CI | 95% Upper CI | Precision |
|---|---|---|---|---|---|
| 80 | 48 | 60.0% | 48.4% | 70.8% | 11.2% |
|  | 52 | 65.0% | 53.5% | 75.4% | 11.0% |
|  | 56 | 70.0% | 58.7% | 79.8% | 10.6% |
|  | 60 | 75.0% | 64.0% | 84.1% | 10.1% |
|  | 64 | 80.0% | 69.5% | 88.2% | 9.4% |
|  | 68 | 85.0% | 75.2% | 92.1% | 8.5% |
|  | 72 | 90.0% | 81.2% | 95.6% | 7.2% |
| 90 | 54 | 60.0% | 49.1% | 70.2% | 10.6% |
|  | 59 | 65.6% | 54.7% | 75.3% | 10.3% |
|  | 63 | 70.0% | 59.4% | 79.3% | 10.0% |
|  | 68 | 75.6% | 65.3% | 84.1% | 9.4% |
|  | 72 | 80.0% | 70.2% | 87.7% | 8.8% |
|  | 77 | 85.6% | 76.5% | 92.1% | 7.8% |
|  | 81 | 90.0% | 81.8% | 95.4% | 6.8% |
| 100 | 60 | 60.0% | 49.7% | 69.7% | 10.0% |
|  | 65 | 65.0% | 54.8% | 74.3% | 9.8% |
|  | 70 | 70.0% | 60.0% | 78.8% | 9.4% |
|  | 75 | 75.0% | 65.3% | 83.2% | 9.0% |
|  | 80 | 80.0% | 70.8% | 87.4% | 8.3% |
|  | 85 | 85.0% | 76.4% | 91.4% | 7.5% |
|  | 90 | 90.0% | 82.3% | 95.1% | 6.4% |

Results and Analysis

The primary outcome of the study was the comparison of benchmark tests for dry eye such as TFBUT, Corneal staining, Schirmer's test, and OSDI questionnaires with results from a test of tear film constituents (e.g., lysozyme).

All collected samples obtained from patients' eyes which met the entry criteria were included in the analyses. The goal of the study was to develop an assessment tool to compare benchmark tests for dry eye with a kit that tests the tear film compound, lysozyme. Data was distributed from lowest to highest values and compared with other parameters to identify positive and negative correlations. FIG. 4 illustrates the correlation of test line intensity with analyte concentration. In some embodiments, a reduced test line intensity correlates with a test for dry eye (e.g., Schirmer's test, corneal staining, OSDI, etc.).

In some embodiments, the correlation of the test line indicates that a lower amount of lysozyme on a test assay according to some embodiments of the present invention, such as, for example, 0 to 1 μg/ml correlates with a lower result as detected by at least one test selected from the group consisting of the Schirmer's test, the corneal staining test, ODSI, and TFBUT.

Sample size in this pilot study (198 total eyes, 98 per group) was not based on any power analysis, but was based on an approximation of the number of eyes sufficient to build a model for a distinguishing between healthy and suspected dry eye tears and evaluation of benchmark standard testing with the different tested parameters.

Adverse Events (AEs) included any events reported over the course of the tear collection and ocular surface assessment procedures. This clinical study involved TFBUT, corneal staining and the collection of tears for the constituent analysis. During these tests the participant may have felt a foreign body sensation. During the tear collection there may have been cases of direct contact with the eye due to movement, resulting in corneal abrasion, or eye redness. Any such events were noted and graded as follows:

Mild: Sign or symptom, usually transient, requiring no special treatment, generally not interfering with usual activities.

Moderate: Sign or symptom, which may be ameliorated by simple therapeutic measures; may interfere with usual activity.

Severe: Sign or symptom that are intense or debilitating and that interfere with usual activities. Recovery was usually aided by therapeutic measures.

A total of 198 subjects completed the study, including 126 women and 72 men. The breakdown of subjects according to entry criteria A or B is outlined in Table 10 below. Those who met entry criteria were not matched for age or gender in this study.

TABLE 10

|  | Men | Women | mean age |
|---|---|---|---|
| Group A Healthy | 41 | 59 | 45.5 |
| Group B Suspected DE | 31 | 67 | 58.6 |

Subjects enrolled in each study group met the entry criteria of either healthy or suspected dry eye. The only demographic criteria that showed a significant difference between the two groups was age; preliminary analysis showed no significant difference in any tear metrics between the two groups. In addition, both groups displayed a range of values for the benchmark testing parameters. Based upon this observation, all subjects were pooled into a single group and analyzed using population quartiles with an assumption that the population sampled represented a continuum of dry eye severity. Using this concept, measurements for each of the benchmark tests were ranked, and mean values for each of 4 quartiles were compared to measures for the tear diagnostics.

Quartile Analysis:

The quartile analysis for TFBUT, inferior staining, and Schirmer's tests are summarized in Table 11. The focus of this approach was on the extremes, quartiles 1 and 4, as these represent those patients with the largest differences for each metric. In all three measures, Q1 was the quartile with values expected for normal patients and Q4 was the quartile with values associated with dry eye disease. For example, those in Q1 have a mean TFBUT of 12.80 seconds and so would be considered normal while those in Q4 have a mean TFBUT of 2.34 seconds, consistent with a diagnosis of moderate dry eye disease. When the mean values for tested parameters in each of the TFBUT-defined quartiles were compared, associations between the break-up time metric and tear constituent dynamics emerged. The decrease in TFBUT between Q1 and Q4 was accompanied by a decrease in lysozyme. Inferior staining increases from Q1 to Q4, and this increase was significantly correlated with an increase in lysozyme. Quartiles defined by Schirmer's scores exhibited significant negative correlations: while the mean Schirmer's score went down from Q1 to Q4, values for lysozyme increases, and showed a significant difference between Q1 and Q4. This negative correlation was due to the nature of the Schirmer's scores, where higher values (Q1) indicated a healthy tear production.

Table 11 shows quartile analysis for TFBUT, inferior staining and Schirmer's Test. T-test values, where significant (<0.05), are highlighted in bold.

TABLE 11

| TFBUT | Mean | n | % of eyes | Mean values Lysozyme |
|---|---|---|---|---|
| Q1 | 12.80 | 48 | 24.6% | 0.734 |
| Q4 | 2.34 | 48 | 24.6% | 0.541 |
| Q4 − Q1 | −10.46 | | | −0.194 |
| Q1 vs. Q4, t test | | | | 0.053 |

| Inferior Staining | Mean | n | % of eyes | Lysozyme |
|---|---|---|---|---|
| Q1 | 0.42 | 52 | 27.5% | 0.434 |
| Q4 | 2.25 | 59 | 31.2% | 0.757 |
| Q4 − Q1 | 1.83 | | | 0.323 |
| Q1 vs. Q4, t test | | | | 0.010 |

| Schirmer's Test | Mean | n | % of eyes | Lysozyme |
|---|---|---|---|---|
| Q1 | 32.44 | 52 | 26.40% | 0.509 |
| Q4 | 5.21 | 52 | 26.40% | 0.797 |
| Q4 − Q1 | −27.23 | | | 0.289 |
| Q1 vs. Q4, t test | | | | 0.002 |

A second round of quartile analysis used the same approach to determine whether quartiles defined by tear constituent values show similar correlations with other metrics of the signs and symptoms of dry eye disease. These data are shown in Table 12.

Table 12. Quartile analysis for lysozyme. T-test values, where significant (<0.05), are highlighted in bold.

TABLE 12

| | Lysozyme Means | N | % of eyes | Mean Values | | | | | |
|---|---|---|---|---|---|---|---|---|---|
| | | | | TFBUT | OSDI | Ora Calibra Ocular Discomfort | Inferior | Corneal Sum | Schirmer's |
| Q1 | 0.00 | 55 | 27.78% | 5.78 | 13.66 | 1.18 | 1.13 | 2.48 | 19.65 |
| Q4 | 1.07 | 104 | 52.53% | 6.56 | 14.77 | 1.25 | 1.41 | 3.18 | 15.38 |
| Q1-Q4 | | | | −0.78 | −1.11 | −0.07 | −0.29 | −0.70 | 4.27 |
| Q1 vs. Q4, t-test | | | | 0.307 | 0.686 | 0.754 | 0.025 | 0.012 | 0.015 |

The lysozyme quartile displayed a significant difference for corneal staining measures, with inferior and total corneal staining showing a positive correlation with increases in protein levels from Q1 to Q4.

Discussion

The current study illustrated the heterogeneity of the two populations of subjects originally enrolled for analysis. Despite their inclusion based upon differential criteria for symptomology, TFBUT, no significant differences between the two populations were identified in the tear constituent analysis. Significant difference was observed for corneal staining and Schirmer's test.

In some embodiments, the method of the present invention provides for a method of measuring dry eye, including tear constituent analysis. In some embodiments, the method of the present invention provides for a method of measuring dry eye, including tear constituent analysis, and comparing tear constituent analysis to tests such as, but not limited to, Schirmer's test, TFBUT, etc., so as to obtain information to treat a patient diagnosed with dry eye disease.

The quartile analyses show the relationships between traditional metrics and the tested parameters which are part of the tear constituents. An exception to this is TFBUT, which shows only modest correlations with any of the measured tear constituents. In contrast, corneal staining measures (such as inferior staining, Table 11) are well-correlated with changes in the tested parameters. This is consistent with a diagnosis of evaporative dry eye, where a reduction in aqueous content of the tears would yield apparent increases in the concentrations of all tear constituents. Alternatively, the increases in tear constituent concentration(s) can result from an inflammatory response to ocular surface distress that initiates a shift in the ratio of serious to mucus lacrimal secretions. Additionally, lysozyme correlates with higher staining and lower Schirmer's scores; however, lysozyme does not show significant correlation with TFBUT.

In some embodiments, the method of the present invention includes the use of at least one diagnostic test. In some embodiments, in performing such a comparison of tear constituents in healthy and dry eye subjects, a multiplicative effect is obtained. In some embodiments, a kit is used to provide an assessment between severe patients and healthy subjects.

Example 3: Measurement of Mucin in Tear Samples According to Some Embodiments of the Present Invention The levels of a prominent tear constituent were examined in healthy subjects and in subjects who met one or more criteria of mild to moderate dry eye. The following experiments illustrate a comparison between benchmark testing for assessment of dry eye with a quantitative measure of a tear constituent. Examples of the tests used to quantitatively measure at least one tear constituent are corneal staining, Schirmer's tests, TFBUT, and provided symptom assessment including the OSDI questionnaire and the Ora-Calibra™ ocular discomfort score. The OSDI is a 12 questions assessment that has become a standard for dry eye symptomology. The Ora-Calibra assessments for discomfort also provide a measurement of symptomology by allowing a patient to answer questions, where the number of questions is reduced compared to the OSDI. Samples of tears were collected using capillary tubes and then underwent analysis for the tear constituent. The tear constituent measured was mucin.

Tear Constituent Assay and Measurement Methodology

Rapid test strips (tear analyzing strips) and reagents were used to measure lactoferrin levels using a semi-quantitative technique; where the semi-quantitative technique followed a fixed running time for each type of assay, strips were scanned with HP's scanner model scanjet 200. The scanned figure was optimized using Function Lighten/Darken: Highlights—(−) 50; Shadows—(−) 69; Midtones—(−) 50; Gamma—1.7 followed by recording of signal intensity (shown in FIG. 5). Determination of the tear constituent was conducted using semi-quantitative estimation of the intensity test lines compared to intensity of a series of control lines.

Experimental Design

Subject Population:

Subjects for the study included anyone over the age of 18 years who met the inclusion and exclusion criteria listed in the following tables. The study population included two groups of subjects (Group A, as shown in Table 1 in Example 1 above, and Group B, shown in Table 2 in Example 1 above) with approximately equal numbers of each (approximately 100 subjects per group):

An exemplary embodiment of the method of the present invention was a prospective, single-center, single-visit, parallel-group, data and tear collection study, consisting of approximately 200 subjects. There was one scheduled study visit where subjects were screened; those who met the eligibility criteria were enrolled in the study.

Tear Sample Collection:

The procedure for tear sample collection was according to the method described in Example 1 above.

Mucin Assay:

The assay allows for detection of the mucin in human tears by detecting sugar groups of mucin (a glycoprotein, i.e. containing at least one sugar moiety) using a Lateral Flow immunochromatographic assay. First, a diluted tear sample was placed on the sample pad. Then, additional drops of washing solution were placed on the sample pad to allow the tear sample to migrate and wet the conjugate pad. The conjugate pad contained a first lectin (e.g., Jacalin) conjugated to gold particles through biotin-Avidin interaction. The conjugated lectin bound the mucin from the tear sample and migrated through the nitrocellulose membrane towards the wick. When the gold conjugate/mucin complexes reached the test zone, the gold conjugate/mucin react with a second lectin (wheat germ agglutinin ("WGA")) fixed to the membrane surface (i.e., at the test line). The accumulation of the gold conjugate/mucin bound to the test line form a pinkish red visible line. An excess amount of complex then migrated to a second zone containing biotin BSA and bound a streptavidin gold conjugate, which formed a second line (a control line). The control line indicated test validity. A residual amount of conjugate and tear sample migrated from the nitrocellulose membrane into the wick pad.

The test strip was produced as follows: 1 mg/ml (0.75-1.5 mg/ml) WGA was impregnated onto a chromatographic membrane of nitrocellulose (e.g., Whatman's paper, FF120). Impregnation is in the shape of a 1 mm wide line. The lectin solution additionally contains the following: (1) buffer, e.g., phosphate buffered saline at pH 7.4 or Tris, HEPES, Borax, or MES buffer with pH value ranging from 6.5-9.0; (2) 2% trehalose or sucrose, ranging from 1%-4% concentration; (3) 1-4% ethanol (e.g., but not limited to, 1%, 2%, 3%, 4% ethanol). The WGA impregnated nitrocellulose was dried at 50 degrees C. for 10 minutes to bind the protein to the nitrocellulose. Binding of the WGA to nitrocellulose can also occur between 37-60 degrees C. for 5 to 24 hours, where a higher temperature would allow for a shorter incubation time. The biotin was bound to Jacalin by conjugating biotin to Jacalin at a ratio of, e.g., but not limited to, 11:1, 22:1, or 33:1. Biotin-Jacalin was bound to streptavidin-gold conjugate at a ratio of 5 µg/ml biotin-Jacalin and between OD0.5/ml-OD2.0/ml, e.g., but not limited to, OD1/ml, gold-streptavidin. The reaction complex can also include wash reagent, which clears excess gold conjugates from the nitrocellulose membrane. The wash reagent can contain the following: (1) PBS×1 at pH 7.4 (can range from pH 7.0-9.0); (2) 1% fatty-acid free bovine serum albumin (can range from 0.5%-3.0%); (3) 0.1% Tween 20 (can range from 0.05%-2.0%); or any combination thereof. Additionally, 0.05% sodium dodecylsulfate may be added to the wash reagent at a concentration from 0.01%-1.0%. Regarding FIG. 5, the line intensity of 1 is formed when mucin is measured at 12.5 µg/ml.

Tear Film Break Up Time Test:

The procedure was carried out according to the method described in Example 1 above.

Corneal Fluorescein Staining:

The procedure was carried out according to the method described in Example 1 above.

Unanesthetized Schirmer's Test:

The procedure was carried out according to the method described in Example 1 above.

Ora Calibra™ Ocular Discomfort Scale:

The procedure was carried out according to the method described in Example 1 above.

Ora Calibra™ Ocular Discomfort & 4-Symptom Questionnaire:

The questionnaire was carried out according to the method described in Example 1 above.

Standards of professional care to protect the ocular safety of subjects were followed with regard to study regimen adherence. Subjects who met entry criteria provided demographic information, medical and ocular history and artificial tears use if appropriate. Clinical staff confirmed that subjects did not use artificial tears in the hour prior to the study, then guided subjects through the following procedures:

1. Subjects completed the OSDI© questionnaire and Ora Calibra™ Ocular Discomfort & 4-symptom Questionnaire.
2. Subjects and staff reviewed source documents to confirm that subject met all inclusion/exclusion criteria based on current medications and medical history.
3. Clinical staff collected 6-25 microliters of tears using a capillary from the right eye of the subject. Staff labeled the collection vial with the subject screening number and emptied the capillary contents into the vial.
4. In the cases where tear volume collected from the right eye was below 6 microliters, a sample was drawn from the left eye and the capillary was emptied into another clean vial marked with same subject screening number.
5. Clinical staff performed tear film break up time test on collection eye(s).
6. Clinical staff performed Corneal Fluorescein Staining and examined the ocular surface of the collection eye(s).
7. If 6 or greater microliters were collected from the right eye, but the subject did not meet Tear Film Break Up Time or Fluorescein Staining inclusion criteria in the right eye, steps 3-6 were repeated in left eye.
8. Clinical staff performed un-anesthetized Schirmer's Test on collection eye(s).
9. Clinical staff reviewed results to determine if patient met all inclusion/exclusion criteria based on data collected according to items 3-8.
10. Patients who met all criteria were assigned a subject study number and categorized on label based on diagnosis of healthy or suspected dry eye patient.
11. Adverse events, if applicable, were documented.

Samples were handled and tested using the following parameters:

1. Volume of collected tears was measured using a micropipette. Twice the measured volume was added with Phosphate Buffer Saline (PBS) for a final dilution of 1:3.
2. Diluted tears were further diluted serially to the following dilutions: 1:50, 1:100 and 1:200 with PBS.
3. Two microliters of diluted sample were mixed with 18 microliters of gold conjugate mix in a microtube. The relevant test strip was dipped in that mix for 4 minutes.
4. Additional 25 microliters of wash solution were added to the tube for excess dye clearance from reaction zone.
5. After 6 minutes developed test strips were gently blot against tissue paper and scanned with a desk scanner.
6. Test intensity was quantified according to the intensity scale presented in FIG. 5.

Power Analysis:

Table 13 presents power for selected sample sizes.

TABLE 13

| Performance Goal | Sample Proportion | N | Power |
|---|---|---|---|
| 0.55 | 0.70 | 95 | 0.82 |
|  | 0.72 | 75 | 0.82 |
|  | 0.75 | 50 | 0.84 |
| 0.60 | 0.70 | 100 | 0.55 |
|  | 0.72 | 100 | 0.71 |
|  | 0.75 | 90 | 0.84 |
| 0.65 | 0.70 | 100 | 0.16 |
|  | 0.72 | 100 | 0.29 |
|  | 0.75 | 100 | 0.55 |

The power was estimated using Exact Binomial method, where two co-primary endpoints (sensitivity and specificity) were taken into account, and where "N" represents the number of positive only (or negative only) cases. Thus, the total sample size was doubled.

Table 14 illustrates a "Precision" parameter, which is defined as a half-length of confidence interval (CI). The CI is an interval estimate of a population parameter. The CI is an observed interval (i.e. it is calculated from the observations), in principle different from sample to sample, that frequently includes the parameter of interest if the experiment is repeated.

TABLE 14

| Sample Size | Obtained Number of Responders | Obtained Rate | 95% Lower CI | 95% Upper CI | Precision |
|---|---|---|---|---|---|
| 80 | 48 | 60.0% | 48.4% | 70.8% | 11.2% |
|  | 52 | 65.0% | 53.5% | 75.4% | 11.0% |
|  | 56 | 70.0% | 58.7% | 79.8% | 10.6% |
|  | 60 | 75.0% | 64.0% | 84.1% | 10.1% |
|  | 64 | 80.0% | 69.5% | 88.2% | 9.4% |
|  | 68 | 85.0% | 75.2% | 92.1% | 8.5% |
|  | 72 | 90.0% | 81.2% | 95.6% | 7.2% |
| 90 | 54 | 60.0% | 49.1% | 70.2% | 10.6% |
|  | 59 | 65.6% | 54.7% | 75.3% | 10.3% |
|  | 63 | 70.0% | 59.4% | 79.3% | 10.0% |

TABLE 14-continued

| Sample Size | Obtained Number of Responders | Obtained Rate | 95% Lower CI | 95% Upper CI | Precision |
|---|---|---|---|---|---|
| | 68 | 75.6% | 65.3% | 84.1% | 9.4% |
| | 72 | 80.0% | 70.2% | 87.7% | 8.8% |
| | 77 | 85.6% | 76.5% | 92.1% | 7.8% |
| | 81 | 90.0% | 81.8% | 95.4% | 6.8% |
| 100 | 60 | 60.0% | 49.7% | 69.7% | 10.0% |
| | 65 | 65.0% | 54.8% | 74.3% | 9.8% |
| | 70 | 70.0% | 60.0% | 78.8% | 9.4% |
| | 75 | 75.0% | 65.3% | 83.2% | 9.0% |
| | 80 | 80.0% | 70.8% | 87.4% | 8.3% |
| | 85 | 85.0% | 76.4% | 91.4% | 7.5% |
| | 90 | 90.0% | 82.3% | 95.1% | 6.4% |

Results and Analysis

The primary outcome of the study was the comparison of benchmark tests for dry eye such as TFBUT, Corneal staining, Schirmer's test, and OSDI questionnaires with results from a test of tear film constituents (e.g., mucin).

All collected samples obtained from patients' eyes which met the entry criteria were included in the analyses. The goal of the study was to develop an assessment tool to compare benchmark tests for dry eye with a kit that tests the tear film compound, mucin. Data was distributed from lowest to highest values and compared with other parameters to identify positive and negative correlations. FIG. 5 illustrates the correlation of test line intensity with analyte concentration. In some embodiments, a reduced test line intensity correlates with a test for dry eye (e.g., Schirmer's test, corneal staining, OSDI, etc.).

In some embodiments, the correlation of the test line indicates that a lower amount of mucin on a test assay according to some embodiments of the present invention, such as, for example, 0 to 1 μg/ml correlates with a lower result as detected by at least one test selected from the group consisting of the Schirmer's test, the corneal staining test, ODSI, and TFBUT.

Sample size in this pilot study (198 total eyes, 99 per group) was not based on any power analysis, but was based on an approximation of the number of eyes sufficient to build a model for a distinguishing between healthy and suspected dry eye tears and evaluation of benchmark standard testing with the different tested parameters.

Adverse Events (AEs) included any events reported over the course of the tear collection and ocular surface assessment procedures. This clinical study involved TFBUT, corneal staining and the collection of tears for the constituent analysis. During these tests the participant may have felt a foreign body sensation. During the tear collection there may have been cases of direct contact with the eye due to movement, resulting in corneal abrasion, or eye redness. Any such events were noted and graded as follows:

Mild: Sign or symptom, usually transient, requiring no special treatment, generally not interfering with usual activities.

Moderate: Sign or symptom, which may be ameliorated by simple therapeutic measures; may interfere with usual activity.

Severe: Sign or symptom that are intense or debilitating and that interfere with usual activities. Recovery was usually aided by therapeutic measures.

A total of 198 subjects completed the study, including 126 women and 72 men. The breakdown of subjects according to entry criteria A or B is outlined in Table 15 below. Those who met entry criteria were not matched for age or gender in this study.

TABLE 15

| | Men | Women | mean age |
|---|---|---|---|
| Group A Healthy | 41 | 59 | 45.5 |
| Group B Suspected DE | 31 | 67 | 58.6 |

Subjects enrolled in each study group met the entry criteria of either healthy or suspected dry eye. The only demographic criteria that showed a significant difference between the two groups was age; preliminary analysis showed no significant difference in any tear metrics between the two groups. In addition, both groups displayed a range of values for the benchmark testing parameters. Based upon this observation, all subjects were pooled into a single group and analyzed using population quartiles with an assumption that the population sampled represented a continuum of dry eye severity. Using this concept, measurements for each of the benchmark tests were ranked, and mean values for each of 4 quartiles were compared to measures for the tear diagnostics.

Quartile Analysis:

The quartile analysis for TFBUT, inferior staining, and Schirmer's tests are summarized in Table 16. The focus of this approach was on the extremes, quartiles 1 and 4, as these represent those patients with the largest differences for each metric. In all three measures, Q1 was the quartile with values expected for normal patients and Q4 was the quartile with values associated with dry eye disease. For example, those in Q1 have a mean TFBUT of 12.80 seconds and so would be considered normal while those in Q4 have a mean TFBUT of 2.34 seconds, consistent with a diagnosis of moderate dry eye disease. When the mean values for tested parameters in each of the TFBUT-defined quartiles and/or corneal staining were compared, associations between the break-up time metric and tear constituent dynamics emerged. The decrease in TFBUT between Q1 and Q4 is accompanied by a decrease in mucin. Quartiles defined by Schirmer's scores show negative correlations, e.g., while the mean Schirmer's score is reduced from Q1 to Q4, the amount of mucin increases. The mucin-defined quartiles show significant correlation with corneal staining scores, and also exhibit a correlation with symptom scores OSDI and Ora Calibra Ocular Discomfort scores. Increased mucin values are correlate with greater symptom scores, stronger corneal staining scores, and reduced Schirmer's scores.

Table 16 shows quartile analysis for TFBUT, inferior staining and Schirmer's Test. T-test values, where significant (<0.05), are highlighted in bold.

TABLE 16

| TFBUT | | | % of | Mean values |
|---|---|---|---|---|
| | Mean | n | eyes | Mucin |
| Q1 | 12.80 | 48 | 24.6% | 0.579 |
| Q4 | 2.34 | 48 | 24.6% | 0.443 |
| Q4 − Q1 | −10.46 | | | −0.135 |
| Q1 vs. Q4, t test | | | | 0.103 |
| Inferior Staining | | | % of | |
| | Mean | n | eyes | Mucin |
| Q1 | 0.42 | 52 | 27.5% | 0.351 |
| Q4 | 2.25 | 59 | 31.2% | 0.646 |
| Q4 − Q1 | 1.83 | | | 0.295 |
| Q1 vs. Q4, t test | | | | 0.003 |

TABLE 16-continued

| Schirmer's Test | | % of | |
|---|---|---|---|
| | Mean | n | eyes | Mucin |
| Q1 | 32.44 | 52 | 26.40% | 0.466 |
| Q4 | 5.21 | 52 | 26.40% | 0.624 |
| Q4 − Q1 | −27.23 | | | 0.158 |
| Q1 vs. Q4, t test | | | | 0.047 |

A second round of quartile analysis used the same approach to determine whether quartiles defined by tear constituent values show similar correlations with other metrics of the signs and symptoms of dry eye disease. These data are shown in Table 17.

Table 17. Quartile analysis for mucin. T-test values, where significant (<0.05), are highlighted in bold.

TABLE 17

| | | | Mean Values | | | | | |
|---|---|---|---|---|---|---|---|---|
| Mucins | | % of | | | Ora Calibra Ocular | | Corneal | |
| | Means | N | eyes | TFBUT | OSDI | Discomfort | Inferior | Sum | Schirmer's |
| Q1 | 0.07 | 55 | 26.77% | 5.30 | 11.26 | 0.98 | 1.08 | 2.45 | 19.68 |
| Q4 | 0.93 | 78 | 39.39% | 6.55* | 17.59 | 1.44 | 1.37 | 3.06 | 15.09 |
| Q1-Q4 | | | | −1.25 | −6.33 | −0.45 | −0.29 | −0.62 | 4.59 |
| Q1 vs. Q4, t-test | | | | 0.106 | 0.044 | 0.018 | 0.062 | 0.011 | 0.015 |

The quartiles associated with lacrimal gland protein mucin displayed a significant difference for corneal staining measures, with inferior and total corneal staining and Schirmer's test showing a positive correlation with increases in protein levels from Q1 to Q4.

Discussion

The current study illustrated the heterogeneity of the two populations of subjects originally enrolled for analysis. Despite their inclusion based upon differential criteria for symptomology, TFBUT and inferior corneal staining, no statistically significant differences between the two populations were identified in the tear constituent analysis.

In some embodiments, the method of the present invention provides for a method of measuring dry eye, including tear constituent analysis. In some embodiments, the method of the present invention provides for a method of measuring dry eye, including tear constituent analysis, and comparing tear constituent analysis to tests such as, but not limited to, Schirmer's test, TFBUT, etc., so as to obtain information to treat a patient diagnosed with dry eye disease.

The quartile analyses show the relationships between traditional metrics and the tested parameters which are part of the tear constituents. An exception to this is TFBUT, which shows only modest correlations with any of the measured tear constituents. In contrast, corneal staining measures (such as inferior staining, Table 16) are well-correlated with changes in the tested parameters. This is consistent with a diagnosis of evaporative dry eye, where a reduction in aqueous content of the tears would yield apparent increases in the concentrations of all tear constituents. Alternatively, the increases in tear constituent concentration(s) can result from an inflammatory response to ocular surface distress that initiates a shift in the ratio of serious to mucus lacrimal secretions.

In some embodiments, the method of the present invention includes the use of at least one diagnostic test. In some embodiments, in performing such a comparison of tear constituents in healthy and dry eye subjects, a multiplicative effect is obtained. In some embodiments, a kit is used to provide an assessment between severe patients and healthy subjects.

Example 4: Measurement of Multiple Constituents of Tear Samples According to Some Embodiments of the Present Invention One approach to develop more reliable diagnostics for DES is a comparative examination of prominent tear constituents in healthy subjects and in DES subjects. Multiple tear components were measured with the goal of determining which measures or combination of measures might show reliable correlations with establish measures of DES, and therefore represent the basis for a new diagnostic modality. In performing this comparison of tear constituents in healthy and DES patients, it was observed that a combination of assays might provide potential for a multiplicative diagnostic effect.

In the study outlined in this Example, subjects underwent commonly used benchmark tests including corneal staining, Schirmer's tests, TFBUT, and symptom assessments using the OSDI questionnaire. These benchmark tests were used to grade the severity of each subjects' disease according to an established scoring matrix used in previous FDA regulatory approval processes for other dry eye syndrome diagnostic products. Tear samples collected from each subject were analyzed using assays for 5 tear constituents with the goal of distinguishing between tears of healthy subjects and tears of subjects with dry eye syndrome. Tear samples underwent quantitative analysis for lysozyme, lactoferrin, matrix metalloproteinase 9, albumin and mucin, each scored on an ordinal scale of 0.1 to 2, with increments of 0.25. Assay results were read by two independent readers as an internal control; in over 98% of the cases, the difference between the readers was insignificant.

The objective of this study outlined in this Example was to assess the effectiveness of the developed assays in tears of healthy subjects as well as subjects with dry eye, based on the FDA definitions as were used in previous FDA regulatory approval processes for other dry eye syndrome products (see inclusion and exclusion criteria below).

This was a prospective, single center, single visit, parallel group, data and tear collection study. There was one scheduled study visit where subjects were screened and if they met eligibility criteria were enrolled in the study. Source documents served as CRFs for study data collected. There was no test article in this study.

Written informed consent was obtained from the subject before any procedure specified by this protocol were initiated, including screening procedures. The original signed informed consent forms were maintained with the subject records for all subjects. Standards of professional care to protect the ocular safety of subjects were followed with regard to study regimen adherence.

Selection of Study Population

The study population was divided into two groups:
Group A: subjects with healthy eyes (Control; Approximately 30 subjects)
Group B: subjects with dry eye syndrome (Grades 1-4; Approximately 40 subjects).

Inclusion and Exclusion Criteria

Inclusion:
In order to be eligible for inclusion, the subjects were:
1. Be at least 30 years of age and may be of any race and either gender;
2. Be able to read, sign, and date the IRB approved informed consent Additionally, the informed consent must be signed and dated by the individual consenting the subject;
3. Agree to allow tear samples to be collected from both eyes;
4. Be willing to follow the study procedures and visit schedule;
5. Meet the applicable severity grade criteria of Negative Control, Grade 1, Grade 2, or Grade 3-4;

Exclusion:
Subjects were excluded if:
1. The subject had an allergy to topical anesthetic or fluorescein dye;
2. The subject had a history of eye injury, trauma, or ocular surgery within the past 3 months;
3. The subject had a known blockage of the lacrimal drainage system;
4. The subject was currently treated medically for a chronic eye syndrome such as glaucoma, allergy or conjunctivitis;
5. The subject had a condition, which in the opinion of the Principal Investigator, would interfere with optimal participation in the study, or which would present a special risk to the subject;
6. The subject had worn contact lenses in the last 7 days;
7. The subject used an investigational study drug or study device within 30 days of enrollment;
8. The subject had previous corneal refractive surgery including RK, LASIK, or PRK surgery;
9. The subject had current active intraocular inflammation or history of intraocular inflammation, e.g. Uveitis.
10. The subject had used oral doxycycline, corticosteroids, or immunomodulators in the last 30 days;
11. The subject had received topical ocular corticosteroids, topical ocular nonsteroidal (NSAIDs) therapy, or topical ocular cyclosporine in the last 30 days;
12. The subject was a female who was pregnant or nursing;
13. The subject had used any topical ophthalmic medications, excluding artificial tears, within 14 days prior to tear collection; or
14. The subject had used any artificial tears within 24 hours of tear collection.

Study Procedures

Severity Grading Scheme: Grading method used to qualify control and dry-eye subjects was based upon the following classification scheme:

TABLE 18

Dry Eye Grading

| Clinical Test | Negative Control | Mild Grade 1 | Moderate Grade 2 | Moderate/ Severe Grade 3 | Severe Grade 4 |
|---|---|---|---|---|---|
| OSDI score | ≤13 | ≥13 | ≥13 | ≥13 | ≥13 |
| TFBUT (sec) | >10 | <10 | ≤10 | ≤5 | $0^a$ |
| Schirmer (mm/5 min) | >10 | <10 | ≤10 | ≤5 | ≤2 |
| Staining (0-5 scale) | 0 | 0 | 1-2 | 3 | ≥4 |

Study Target Enrollment:
The enrollment by subject grades was as follows:
Negative Control: Approximately 30 subjects
Grade 1: Approximately 5 subjects
Grade 2: Approximately 5 subjects
Grade 3-4: Approximately 30 subjects.

Visits and Examinations:
Visit 1 (Baseline and tear collection):
1. Obtained demographic information, medical and ocular history and artificial tears use if appropriate.
2. Instructed the subject to complete the OSDI© questionnaire and Ora Calibra™ Ocular Discomfort & 4-symptom Questionnaire.
3. Performed Visual Acuity.
4. Performed Slit Lamp Exam.
5. Performed Meibomian Gland Assessment on both eyes.
6. Collected 6-25 microliters of tears using a capillary from the right eye of the subject.
7. Performed tear film break up time test on collection eye(s).
8. Performed Corneal Fluorescein Staining and examined the ocular surface on collection eye(s).
9. Performed unanesthetized Schirmer's Test on collection eye(s).
10. Assigned subject study number, record on label based on diagnosis grade.
11. Documented any adverse events, if applicable.

Visit 2 Procedures:
If a subject's Visit 1 tears could not be analyzed (Ex. insufficient volume), subjects were asked to return for a second visit to collect tears.
1. Performed Visual Acuity.
2. Performed Slit Lamp Exam.
3. Collected 6-25 microliters of tears using a capillary from the qualified eye(s) of the subject.

Analysis and Safety Variables

Tear Measurements:
The sum measures from tears of lysozyme, lactoferrin, matrix metalloproteinase 9, albumin and mucin were analyzed as explanatory variables graded in visual line intensity scale of 0.1 to 2 with increments of 0.25 in a logistic regression to determine association with a grade 1-4 dry eye subjects or healthy subjects.

Tear constituents were analyzed in a univariate fashion for association with dry eye. A forward selection procedure was used where after the initial explanatory variable was placed in the model, then additional main effect terms (which were significant within a univariate analysis at a 2-sided alpha=0.10) would be placed in the model as well as the corresponding two-way interaction terms with the other main effects already in the model, terms were added and kept at a 2-sided alpha=0.05. If an interaction term met criteria to be added, then the main effect term was also added.

Dry Eye Assessments:

Subjects were screened for signs and symptoms of dry eye syndrome as described above.

TABLE 19

Enrolled Subject Demographics

|  | Healthy Subjects | Dry Eye Subjects | | | |
|---|---|---|---|---|---|
|  |  | Grade 1 | Grade 2 | Grade 3 | Grade 4 |
| Total | 30 | 5 | 5 | 33 | 1 |
| % non-white | 10 | 0 | 0 | 0 | 0 |
| % female | 50 | 100 | 80 | 75.6 | 0 |
| Age, range | 31-80 | 44-63 | 64-80 | 39-79 | 68 |
| Age, mean ± SD | 48.5 ± 11.4 | 51.2 ± 7.6 | 71.4 ± 5.9 | 61.1 ± 9.3 | — |

Results

A total of 74 subjects completed the study, including 5 each classified as Grade 1 or Grade 2 dry eye, 34 subjects with a Grade of 3 or 4, and 30 healthy controls. Demographics are summarized in Table 5-2. Subjects with dry eye syndrome were more likely to be female (34/44 for grade 3/4 subjects versus 15/30 for controls) and more likely to be older.

Results of the Initial Screens:

Results from tear constituent analysis showed that in a Univariate Wald Chi-squared analysis for each, only albumin showed significant (P less than 0.05) correlation with summated dry eye scores (P=0.0370).

Tear Analysis Result Modeling:

A total of 74 subjects, 44 with grade 1-4 dry eye and 30 healthy, were included in development of predictive models. As a first step in this process, a predictive algorithm based upon albumin measures was built. The model with albumin alone is:

TABLE 20

Model 0 - Albumin alone

|  | DF | Standard Estimate | Error | Wald Chi-Square | Pr > ChiSq |
|---|---|---|---|---|---|
| Intercept | 1 | −0.6491 | 0.5421 | 1.4338 | 0.2311 |
| Albumin | 1 | 1.1142 | 0.5342 | 4.3506 | 0.0370 |

Using these terms, the probability of being a dry eye (Grade 1-4) subject given tear albumin score is calculated as:

$$\frac{\exp(-0.6491 - 1.1142 * \text{Albumin})}{1 + \exp(-0.6491 - 1.1142 * \text{Albumin})}$$

After calculating this probability, a subject was assigned to a group (dry eye or healthy) based on the probability. Using a cutoff probability of 50%, the model correctly classified dry eye subjects as having dry eye 34/44=77.4% of time and correctly classified healthy subjects as healthy 9/30=30.0% of the time.

After increasing the cutoff probability to 60%, the model correctly classified dry eye subjects as having dry eye 30/44=68.2% of time and correctly classified healthy subjects as healthy 19/30=63.3% of the time.

In a combined model, all variables were entered into the model along with every two-way interaction; a backward selection procedure was implemented to remove terms that were non-significant at a 2-sided alpha=0.10. If an interaction term met criteria to be added, then the main effect terms were also required. As the number of Hispanic/Latino subjects was small, model fitting was in issue including ethnicity in the model. Therefore, ethnicity and all two-way interactions thereof were removed.

The resulting model yielded Albumin, Lactoferrin, Age, Gender and Albumin*Lactoferrin as significant explanatory variables and has the following maximum likelihood estimates for the estimating the log odds of the subject being a grade 3/4 dry eye subject:

TABLE 21 model 1 - Albumin/Lactoferrin + Demographics

|  | DF | Standard Estimate | Error | Wald Chi-Square | Pr > ChiSq |
|---|---|---|---|---|---|
| Intercept | 1 | −4.4755 | 2.2037 | 4.1247 | 0.0423 |
| Lactoferrin | 1 | −10.2477 | 4.8174 | 4.5250 | 0.0334 |
| Albumin | 1 | −1.9616 | 1.4646 | 1.7938 | 0.1805 |
| Age | 1 | 0.1263 | 0.0374 | 11.376 | 0.0007 |
| gender (F) | 1 | 1.0347 | 0.3566 | 8.4180 | 0.0037 |
| Lactoferrin*Albumin | 1 | 8.7859 | 4.7024 | 3.4909 | 0.0617 |

Based upon this model the probability of being a dry eye (G1-4) subject given Albumin, Lactoferrin, Age, and Gender scores is calculated with the expression below:

$$\frac{\exp\begin{pmatrix}-5.7198 - 3.9059*\text{Albumin} - 0.7375*\text{Lysozyme} - \\ 2.7929*\text{Lactoferrin} + 0.1507*\text{Age}(yrs) + 1.2206* \\ (-1 \text{ if male}) + 7.1682*\text{Albumin}*\text{Lactoferrin} + 4.4090* \\ \text{Albumin}*\text{Lysozyme} - 10.7566*\text{Lysozyme}*\text{Lactoferrin}\end{pmatrix}}{1 + \exp\begin{pmatrix}-5.7198 - 3.9059*\text{Albumin} - 0.7375*\text{Lysozyme} - \\ 2.7929*\text{Lactoferrin} + 0.1507*\text{Age}(yrs) + 1.2206* \\ (-1 \text{ if male}) + 7.1682*\text{Albumin}*\text{Lactoferrin} + \\ 4.4090*\text{Albumin}*\text{Lysozyme} - \\ 10.7566*\text{Lysozyme}*\text{Lactoferrin}\end{pmatrix}}$$

After calculating this probability, one then a subject was assigned to a group (dry eye or healthy) based on the probability. Using a cutoff probability of 50%, the model correctly classified dry eye subjects as having dry eye 39/44=88.6% of time and correctly classified healthy subjects as healthy 23/30=76.7% of the time.

After increasing the cutoff probability to 55%, the model correctly classified dry eye subjects as having dry eye 37/44=84.1% of time and correctly classified healthy subjects as healthy 24/30=80.0% of the time.

Further increasing the cutoff probability to 60%, the model correctly classified dry eye subjects as having dry eye 36/44=81.8% of time and correctly classified healthy subjects as healthy 26/30=86.7% of the time.

The results of this model demonstrated that choosing either a cutoff probability of 55% or 60% yield sensitivity and specificity greater than or equal to 80%.

Addition of lysozyme alone to Model 1 did not yield any differences in sensitivity or specificity of the model. In contrast, adding interaction terms Lysozyme*Albumin and Lysozyme*Lactoferrin did yield additional predictive power due to the interaction terms, and so a second model was constructed combining all of these terms.

TABLE 22

Model 2 - Albumin/Lysozyme/Lactoferrin/Demographics

|  | DF | Standard Estimate | Error | Wald Chi-Square | Pr > ChiSq |
|---|---|---|---|---|---|
| Intercept | 1 | −5.7198 | 2.9654 | 3.7204 | 0.0538 |
| Albumin | 1 | −3.9059 | 2.0031 | 3.8022 | 0.0512 |
| Lysozyme | 1 | −0.7375 | 3.1381 | 0.0552 | 0.8142 |
| Lactoferrin | 1 | −2.7929 | 5.1812 | 0.2906 | 0.5899 |
| Age | 1 | 0.1507 | 0.0440 | 11.7043 | 0.0006 |
| gender (F) | 1 | 1.2206 | 0.4076 | 8.9656 | 0.0028 |
| Albumin*Lactoferrin | 1 | 7.1682 | 4.4899 | 2.5488 | 0.1104 |
| Albumin*Lysozyme | 1 | 4.4090 | 2.9299 | 2.2644 | 0.1324 |
| Lysozyme*Lactoferrin | 1 | 10.7566 | 7.2803 | 2.1830 | 0.1395 |

Using a cutoff probability of 50%, the model correctly classified dry eye subjects as having dry eye 40/44=90.9% of time and correctly classified healthy subjects as healthy 23/30=76.7% of the time.

After increasing the cutoff probability to 55%, the model correctly classified dry eye subjects as having dry eye 38/44=86.4% of time and correctly classified healthy subjects as healthy 26/30=86.7% of the time.

Further increasing the cutoff probability to 60%, the model correctly classified dry eye subjects as having dry eye 36/44=81.8% of time and correctly classified healthy subjects as healthy 27/30=90.0% of the time.

The addition of lysozyme and the interactions of lysozyme*albumin and lysozyme*lactoferrin improves the sensitivity and specificity slightly at each cutoff probability.

There were no reported adverse events or safety concerns in the course of the study.

Discussion and Overall Conclusion

The purpose of the study outline in this Example was to assess the effectiveness of the methods of the present invention in tears of healthy subjects as well as subjects with dry eye syndrome. First, a standardized grading system was used to define and distinguish populations of healthy subjects from those with different grades of dry eye syndrome. This grading scheme was a composite of four established benchmark tests for assessment of signs and symptoms of dry eye. This definition has been used previously in the U.S. regulatory clinical trial and an FDA approval process of an in-office dry eye screening test called InflammaDry®, a test based upon detection of tear MMP9 levels.

Study subjects graded using the standardized system were also assayed for a panel tear constituents selected based upon their potential to provide an objective measure of dry eye severity. The observed line intensities and subject demographics data were used to build predictive statistical models as a means to judge which developed assays might provide the best diagnostic power.

Results of the developed assays suggested that albumin was the best assay upon which to base a predictive model, as it showed the highest effectiveness to identify DES subjects. Inclusion of additional assays, however, provides the opportunity for even greater sensitivity and specificity. For this reason, and due to the fact that we know that the DES is a multi-factorial syndrome, we performed all our assays and then combined them in a model to ask the question, given the tear constituent score(s) of each subject, how sensitive and how specific can a combination of these constituents be in terms of their ability to diagnose DES.

The test sensitivity represents the number of subjects correctly identified as having DES, while the specificity represents the number of subjects correctly identified as healthy controls. These values can be combined in the positive predictive value (PPV), a measure of what fraction of those subjects identified as DES patients have dry eye. An ideal test would have both a high sensitivity and a high specificity. Table 23 presents a comparison of the sensitivity and specificity of the different models, based upon the results of the different assays.

As for today there are two main DES diagnostic commercial tests in the market, both related to heterogeneous of the patient population and relaying on a single parameter and trying to diagnose multi-factorial disease—The InflammaDry®, a point of use diagnostic that provides a positive or negative assay for the inflammatory marker MMP914 and the TearLab® system which provides a numerical output of tear osmolarity over a range between 302 and 328 mOsm, a range which includes both normal and hyper-osmolar values. The InflammaDry® device and the TearLab® Osmolarity System offer objective diagnostic tests designed for use in the setting of an outpatient office visit; both performed well in sponsored clinical trials.

TABLE 23

Comparison of Models

| MODEL | CUTOFF PROBABILITY | DRY EYE SUBJECTS Sensitivity | HEALTHY SUBJECTS Specificity | POSITIVE PREDICTIVE VALUE |
|---|---|---|---|---|
| MODEL 0 | 50% | 77.4% | 30% | 72.1% |
| albumin | 60% | 68.2% | 63.3% | 65% |
| MODEL 1 | 50% | 88.6% | 76.7% | 79.6% |
| albumin/lactoferrin + | 55% | 84.1% | 80% | 80.8% |
| demographics | 60% | 81.8% | 86.7% | 86% |
| MODEL 2 | 50% | 90.9% | 76.7% | 78.8% |
| albumin/lysozyme/ | 55% | 86.4% | 86.7% | 86.7% |
| lactoferrin/demographics | 60% | 81.8% | 90% | 89.1% |

The sensitivity and specificity values from Model 2 (Table 7-1) are in one line with the commercial diagnostics including the TearLab® Osmolarity system or InflammaDry® (Table 24). This result supports the potential use of Model 2 combined assays as diagnostics for dry eye. Of particular note, the grading scheme for InflammaDry® studies uses the same set of diagnostic criteria for dry eye employed in this study14, a major variable in comparisons of different test performance.

The study results also show that Model 2 is able to diagnose dry eye with sensitivity and specificity superior also to well established existing tests, in particular tests that would normally be conducted in the setting of a clinician's office: Schirmer's Test, TFBUT, symptomatic questionnaires (such as ODSI), or corneal staining.

TABLE 24

Characteristics of Other Dry Eye Tests

| TEST (S) | DRY EYE SUBJECTS Sensitivity | HEALTHY SUBJECTS Specificity |
|---|---|---|
| SCHIRMER'S TEST | 42% | 76% |
| TEAR FILM BREAK-UP TIME | 92% | 17% |
| CORNEAL STAINING | 63% | 89% |
| QUESTIONNAIRE | 89% | 72% |
| INFLAMMADRY ® (MMP9) | 66-97% | 97-98% |
| TEARLAB ® (OSMOLARITY)[17-19] | 64-73% | 71-92% |

While both the InflammaDry® and the TearLab® devices have demonstrated good sensitivity and specificity in some trials, in both cases there is debate as to their overall reliability as diagnostics, mainly due to the fact that both tests are related to heterogeneous of the patient population and relaying on a single parameter trying to diagnose multi-factorial disease. For example, several recent studies have concluded that there was no correlation between Tear-Lab®-based osmolarity measures and other signs or symptoms of dry eye. Similarly, while the initial assessments of InflammaDry® rated it with a high sensitivity and specificity, more recent studies found little or no correlation with results from the MMP9 detection device and other dry eye tests. This difference may be attributed to the differences in sample collection methods.

Both the TearLab® system and the current study collect the tear fluid gently from the lateral aspect of the eye. In contrast, InflammaDry® sampling involves a relatively aggressive rubbing of the lower lid. Direct comparison of MMP9 levels using the two collection methods might be necessary to resolve the basis for the difference in MMP9 findings.

As a further test of the models derived from this study, a dataset from DiagnosTear first clinical trial, which included suspected healthy and DES patients (recruited according to different inclusion criteria) was tested using Model 2; results are shown in Table 25.

TABLE 25

Testing Models on First Clinical Trial Results

| MODEL | CUTOFF PROBABILITY | DRY EYE SUBJECTS Sensitivity | HEALTHY SUBJECTS Specificity |
|---|---|---|---|
| MODEL 2 | 50% | 73.5% | 63% |
| Results using data | 55% | 70.4% | 65% |
| from first clinical trial | 60% | 67.4% | 67% |

It may be valuable to test larger populations or other dry eye grading schemes as a test of the models developed in this study. For example, a grading scheme that includes a conjunctival staining component has been used in recent studies of tear protein proteomics. In addition, the sample sized used for the study may introduce a bias due to the age and gender differences in the subject groups, but this is an issue that can be addressed in future tests.

Inflammation is a known factor in the etiology of dry eye, and tissues exposed to pro-inflammatory signals respond with increases in vascular permeability and exudative fluid loss from the local vasculature. Such exudate can impact the tear film composition with increased electrolyte concentration (i.e., increased osmolarity) and a rise in albumin concentration. Thus, the markers used in this study allow for an integrated measure of several sequela of the dry eye phenotype.

The use of albumin as a diagnostic has a solid scientific rationale. Albumin diffuses out of dilated conjunctival vessels into the tear film, the concentration of which increases during eye closure and wounding. Tear levels of albumin, therefore, can be considered a marker of ocular surface integrity. In addition, one of the hallmark responses in any inflammatory event is an increase in vascular permeability, and with that increase it is reasonable to expect an increase in the flow of soluble components in circulating plasma (where albumin concentrations range from 3 to 5%) from the vasculature out into the tear film. The results of this trial (and other studies) confirm that significant changes in tear film albumin do correlate with dry eye.

There are no reports to date that demonstrate any clear physiological role for albumin in tears. Despite this, preclinical studies of ocular inflammation led Shimura et al (2003) to suggest that albumin in the tear film might represent a compensatory response to reductions in soluble mucins following reduced lacrimation or a loss of goblet cells. The study showed that albumin appears to decrease apoptosis of epithelial cells in rats, suggesting an active role for the serum-derived protein in response to ocular inflammation. They also suggested that tear albumin was a specific marker of ocular surface integrity, a concept that is supported by the findings of DiagnosTear's first clinical study in which a significant positive correlation between albumin and corneal staining was observed.

The results derived from albumin alone (Model 0) are less robust than those which employ multiple assays, but may benefit from the simplicity of measuring only a single tear component, where the potential for procedural or assays interference issues are minimized. In contrast, it may also be worthwhile to examine the diagnostic power of multi-assays models in subjects with low scores on OSDI surveys who are asymptomatic but meet dry eye criteria based upon staining and other traditional dry eye tests. These subjects are at particular risk for ocular surface damage because of their low levels of discomfort.

A potential role of lysozyme and lactoferrin in dry eye has been established for some time, as they are known lacrimal gland products and two of the main components of the healthy aqueous phase of the tear film. Levels of these proteins represent a measure of lacrimal gland production and so any alteration in their concentrations in the tear film would imply a lacrimal gland dysfunction. Other markers in the tears include inflammatory products such as MMP9; such tear markers reflect local, peri-lacrimal infiltration of inflammatory cells.

To the best of our knowledge, we demonstrate, for the first time, that combination of protein levels originated for different locations in the eye have a significant ability to diagnose DES. A test that combines changes in one or more of these two tear constituents with albumin will be sampling two distinct physiological responses to ocular surface challenge, and thus may be able to provide a more robust diagnostic output.

Results from this study confirm that a multi-assay approach is likely to provide the best diagnostic tool for use in the identification and treatment of dry eye syndrome.

The levels of a prominent tear constituent were examined in healthy subjects and in subjects who met one or more criteria of mild to moderate dry eye. The following experiments illustrate a comparison between benchmark testing for assessment of dry eye with a quantitative measure of a tear constituent. Examples of the tests used to quantitatively measure at least one tear constituent are corneal staining, Schirmer's tests, TFBUT, and provided symptom assessment including the OSDI questionnaire and the Ora-Calibra™ ocular discomfort score. The OSDI is a 12 questions assessment that has become a standard for dry eye symptomology. The Ora-Calibra assessments for discomfort also provide a measurement of symptomology by allowing a patient to answer questions, where the number of questions is reduced compared to the OSDI. Samples of tears were collected using capillary tubes and then underwent analysis for the tear constituent. The tear constituent measured was mucin.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method, the method comprising:
   a. obtaining a tear sample from a subject;
   b. determining the level of human serum albumin in the tear sample;
   c. from the determined level of human serum albumin, assigning a score for the determined amount of human serum albumin; and
   d. from the assigned score, calculating a cutoff probability score, according to the following equation:

$$\frac{\exp(-0.6491 - 1.1142 * \text{Albumin})}{1 + \exp(-0.6491 - 1.1142 * \text{Albumin})}$$

wherein if the calculated cutoff probability score is from 50% to 60%, the subject has an ocular surface disorder; and
   e. treating the subject.

2. The method of claim 1, wherein the step of determining the level of human serum albumin in the tear sample, is carried out using a device, the device comprising:
   a. a test strip configured to receive the tear sample from the subject; and
   b. one or more reagent pads comprising reagents, wherein the reagents upon contact with the tear sample, undergo a reaction configured to produce a color, wherein the intensity of the color is proportional to the amount of human serum albumin in the tear sample, and
   wherein the test strip is configured to deliver the tear sample to the one or more reagent pads.

3. The method of claim 1, wherein the ocular surface disorder comprises dry eye disorder.

4. The method of claim 1, wherein the ocular surface disorder comprises an inflammatory event of the eye.

5. The method of claim 1, wherein the method determines ocular surface integrity.

6. The method of claim 1, wherein the method has a cutoff probability score of 50% and correctly classifies subjects as having dry eye 88% of time and correctly classifies subjects as healthy 76% of the time.

7. The method of claim 1, wherein the method has a cutoff probability score of 55% and correctly classifies subjects as having dry eye 84% of time and correctly classifies subjects as healthy 80% of the time.

8. The method of claim 1, wherein the method has a cutoff probability score of 60% and correctly classifies subjects as having dry eye 81% of time and correctly classifies subjects as healthy 86% of the time.

* * * * *